US012676235B2

(12) United States Patent
Fedorov et al.

(10) Patent No.: US 12,676,235 B2
(45) Date of Patent: Jul. 7, 2026

(54) ARTIFICIAL INTELLIGENCE TRAINED WITH OPTICAL MAPPING TO IMPROVE DETECTION OF CARDIAC ARRHYTHMIA SOURCES

(71) Applicants: Skolkovo Institute of Science and Technology, der. Skolkovo (RU); Ohio State Innovation Foundation, Columbus, OH (US)

(72) Inventors: Vadim Valerievich Fedorov, Columbus, OH (US); Brian Hansen, Columbus, OH (US); Alexander Markovich Zolotarev, Moscow (RU); Dmitry Vladimirovich Dylov, Moscow (RU); Ekaterina Alekseevna Ivanova, Moscow (RU); Maxim Valerievich Fedorov, Moscow (RU)

(73) Assignees: Skolkovo Institute of Science and Technology, der. Skolkovo (RU); Ohio State Innovation Foundation

( * ) Notice: Subject to any disclaimer, the term of this patent is extended or adjusted under 35 U.S.C. 154(b) by 1182 days.

(21) Appl. No.: 17/611,501

(22) PCT Filed: May 6, 2020

(86) PCT No.: PCT/RU2020/050089
§ 371 (c)(1),
(2) Date: Nov. 15, 2021

(87) PCT Pub. No.: WO2020/226534
PCT Pub. Date: Nov. 12, 2020

(65) Prior Publication Data
US 2022/0346856 A1 Nov. 3, 2022

Related U.S. Application Data

(60) Provisional application No. 62/843,800, filed on May 6, 2019.

(51) Int. Cl.
*G16H 50/20* (2018.01)
*A61B 5/361* (2021.01)
(Continued)

(52) U.S. Cl.
CPC ............. *G16H 50/20* (2018.01); *A61B 5/361* (2021.01); *G06N 20/00* (2019.01);
(Continued)

(58) Field of Classification Search
CPC .................... G16H 50/20; A61B 5/361; A61B 2018/00351; A61B 2018/00357;
(Continued)

(56) References Cited

U.S. PATENT DOCUMENTS 8,010,186 B1 * 8/2011 Ryu ..................... A61B 5/6852
600/509
2004/0059237 A1 3/2004 Narayan et al.
(Continued)

OTHER PUBLICATIONS

Hansen et al., Human Atrial Fibrillation Drivers Resolved with Integrated Functional and Structural Imaging to Benefit Clinical Mapping, 2018, JACC Clinical Electrophysiology, pp. 1-14. (Year: 2018).*

(Continued)

*Primary Examiner* — Catherine M Voorhees
(74) *Attorney, Agent, or Firm* — Meunier Carlin & Curfman LLC

(57) ABSTRACT

Disclosed are various embodiments of methods, components and systems configured to determine a location of a source of cardiac arrhythmia in a patient's heart. In some embodiments, to determine a source location, electrogram signals are acquired from a region of the patients' heart using a first set of electrodes; and then a pre-trained artificial intelligence (AI) model is applied to predict the location of the cardiac arrhythmia source by using the signals. Importantly, pre- (Continued)

A Predicted Heat Map
HD Catheter, Heart 536562

B Real Labels training of the AI model comprises acquiring electrogram signals from explanted human hearts, the signals are generated by a second set of electrodes assembled into an electrode array that covers at least a part of the explanted human heart, and acquiring co-registered functional and/or structural imaging data in the part of the explanted human heart covered with the electrode array, wherein the functional and/or structural imaging data provide location of at least one source of cardiac arrhythmia.

11 Claims, 15 Drawing Sheets

(51) Int. Cl.
   *G06N 20/00*          (2019.01)
   *A61B 18/00*          (2006.01)
(52) U.S. Cl.
   CPC .............. *A61B 2018/00351* (2013.01); *A61B 2018/00357* (2013.01); *A61B 2018/00577* (2013.01); *A61B 2018/00839* (2013.01)
(58) Field of Classification Search
   CPC .......... A61B 2018/00577; A61B 5/347; A61B 5/7264; A61B 5/7267; G06N 20/00
   See application file for complete search history.

(56)                References Cited

U.S. PATENT DOCUMENTS

| | | | | |
|---|---|---|---|---|
| 2008/0004904 | A1 | 1/2008 | Tran | |
| 2008/0021336 | A1* | 1/2008 | Dobak, III ........... | A61B 5/1102 |
| | | | | 600/508 |
| 2015/0164349 | A1 | 6/2015 | Gopalakrishnan et al. | |
| 2015/0327837 | A1 | 11/2015 | Qi et al. | |
| 2020/0405168 | A1* | 12/2020 | Gabrin ................... | A61B 5/346 |
| 2020/0405393 | A1* | 12/2020 | Villongco ................ | A61B 5/35 |
| 2022/0061732 | A1* | 3/2022 | Krummen ............ | A61B 5/0036 |

OTHER PUBLICATIONS

Attia et al. An artificial intelligence-enabled ECG algorithm for the identification of patients with atrial fibrillation during sinus rhythm: a retrospective analysis of outcome prediction. Lancet 2019; 394:861-867.
Csepe et al. Atrial fibrillation driver mechanisms: Insight from the isolated human heart. Trends Cardiovasc Med 2017; 27:1-11.
Dehghani et al. A Quantitative Comparison of Overlapping and Non-Overlapping Sliding Windows for Human Activity Recognition Using Inertial Sensors. Sensors (Basel) 2019; 19.
European Patent Office. Extended European Search Report. Issued in EP Application No. 20802999.1 on Nov. 23, 2022. 6 pages.
Fedorov et al. Effects of KATP channel openers diazoxide and pinacidil in coronary-perfused atria and ventricles from failing and non-failing human hearts. J Mal Cell Cardiol 2011; 51:215-225.
Filippou et al. Recent advances on the development of phantoms using 3D printing for imaging with CT, MRI, PET, SPECT, and ultrasound. Med Phys 2018.
Hannun et al. Cardiologist-level arrhythmia detection and classification in ambulatory electrocardiograms using a deep neural network. Nat Med 2019; 25:65-69.

Hansen et al. Atrial fibrillation driven by micro-anatomic intramural re-entry revealed by simultaneous sub-epicardial and sub-endocardial optical mapping in explanted human hearts. Eur Heart J 2015; 36:2390-2401.
Hansen et al. Maintenance of Atrial Fibrillation: Are Reentrant Drivers With Spatial Stability the Key? Circ Arrhythm Electrophysiol 2016; 9:e004398.
Hansen et al. First In Vivo Use of High-Resolution Near-Infrared Optical Mapping to Assess Atrial Activation During Sinus Rhythm and Atrial Fibrillation in a Large Animal Model. Circ Arrhythm Electrophysiol 2018; 11 :e006870.
Hansen et al. Human Atrial Fibrillation Drivers Resolved with Integrated Functional and Structural Imaging to Benefit Clinical Mapping. JACC Clin Electrophysiol 2018; 4:1501-1515.
Herron et al. Optical imaging of voltage and calcium in cardiac cells & tissues. Circ Res 2012; 110:609-23.
Kuklik et al. Reconstruction of instantaneous phase of unipolar atrial contact electrogram using a concept of sinusoidal recomposition and Hilbert transform. IEEE Trans Biomed Eng 2015; 62:296-302.
Le Guennec et al. Data Augmentation for Time Series Classification using Convolutional Neural Networks. In: ECML/PKDD Workshop on Advanced Analytics and Learning on Temporal Data 2016. https://halshs.archives-ouvertes.fr/halshs- 01357973. 9 pages.
Li et al. Adenosine-Induced Atrial Fibrillation: Localized Reentrant Drivers in Lateral Right Atria due to Heterogeneous Expression of Adenosine A1 Receptors and GIRK4 Subunits in the Human Heart. Circulation 2016; 134:486-498.
Liang et al. Comparison of Left Atrial Bipolar Voltage and Scar Using Multielectrode Fast Automated Mapping versus Point-by-Point Contact Electroanatomic Mapping in Patients With Atrial Fibrillation Undergoing Repeat Ablation. J Cardiovasc Electrophysiol 2017; 28:280-288.
Lou et al. Tachy-brady arrhythmias: The critical role of adenosine-induced sino-atrial conduction block in post-tachycardia pauses. Heart Rhythm 2013; 10:110-118.
McGillivray et al. Machine learning methods for locating re-entrant drivers from electrograms in a model of atrial fibrillation. R Soc Open Sci 2018; 5:172434.
O'Shea et al. Cardiac Optogenetics and Optical Mapping—Overcoming Spectral Congestion in All-Optical Cardiac Electrophysiology. Front Physiol 2019; 10:182.
Roney et al. Spatial Resolution Requirements for Accurate Identification of Drivers of Atrial Fibrillation. Circ Arrhythm Electrophysiol 2017; 10:e004899.
Terricabras et al. Ablation of persistent atrial fibrillation: Challenges and solutions. J Cardiovasc Electrophysiol 2019. pp. 1809-1821.
Vijayakumar et al. Methodology Considerations in Phase Mapping of Human Cardiac Arrhythmias. Circ Arrhythm Electrophysiol 2016; 9:e004409.
Xiong et al. ECG signal classification for the detection of cardiac arrhythmias using a convolutional recurrent neural network. Physiol Meas 2018; 39:094006.
Zhao et al. Integration of High-Resolution Optical Mapping and 3-Dimensional Micro-Computed Tomographic Imaging to Resolve the Structural Basis of Atrial Conduction in the Human Heart. Circ Arrhythm Electrophysiol 2015; 8:1514-7.
Zhao et al. Three-dimensional Integrated Functional, Structural, and Computational Mapping to Define the Structural "Fingerprints" of Heart-Specific Atrial Fibrillation Drivers in Human Heart Ex Vivo. J Am Heart Assoc 2017; 6.
International Searching Authority (ISA/RU). International Search Report and Written Opinion, issued in PCT Application No. PCT/RU2020/050089 on Sep. 3, 2020. 6 pages.

* cited by examiner

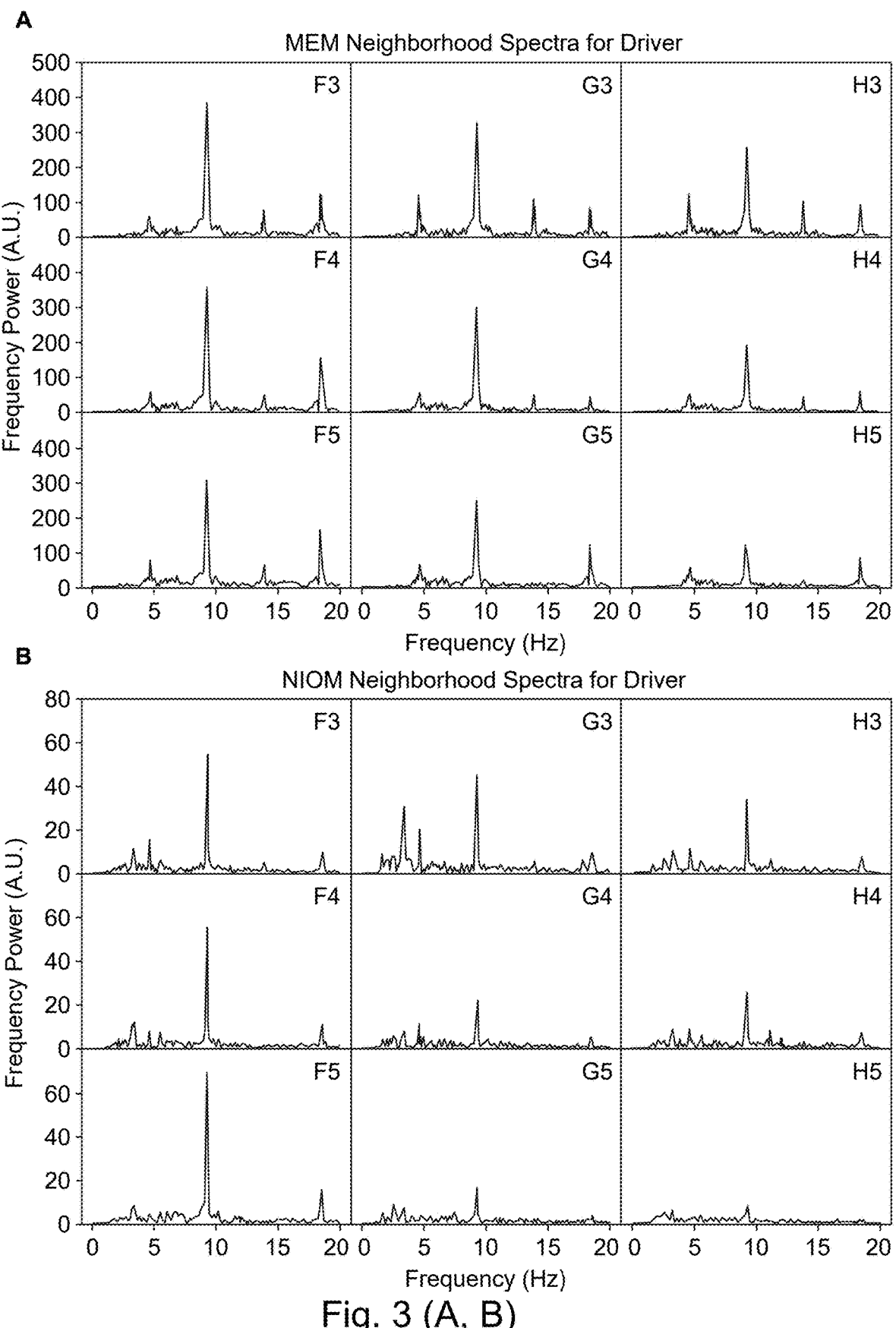
Fig. 3 (A, B)

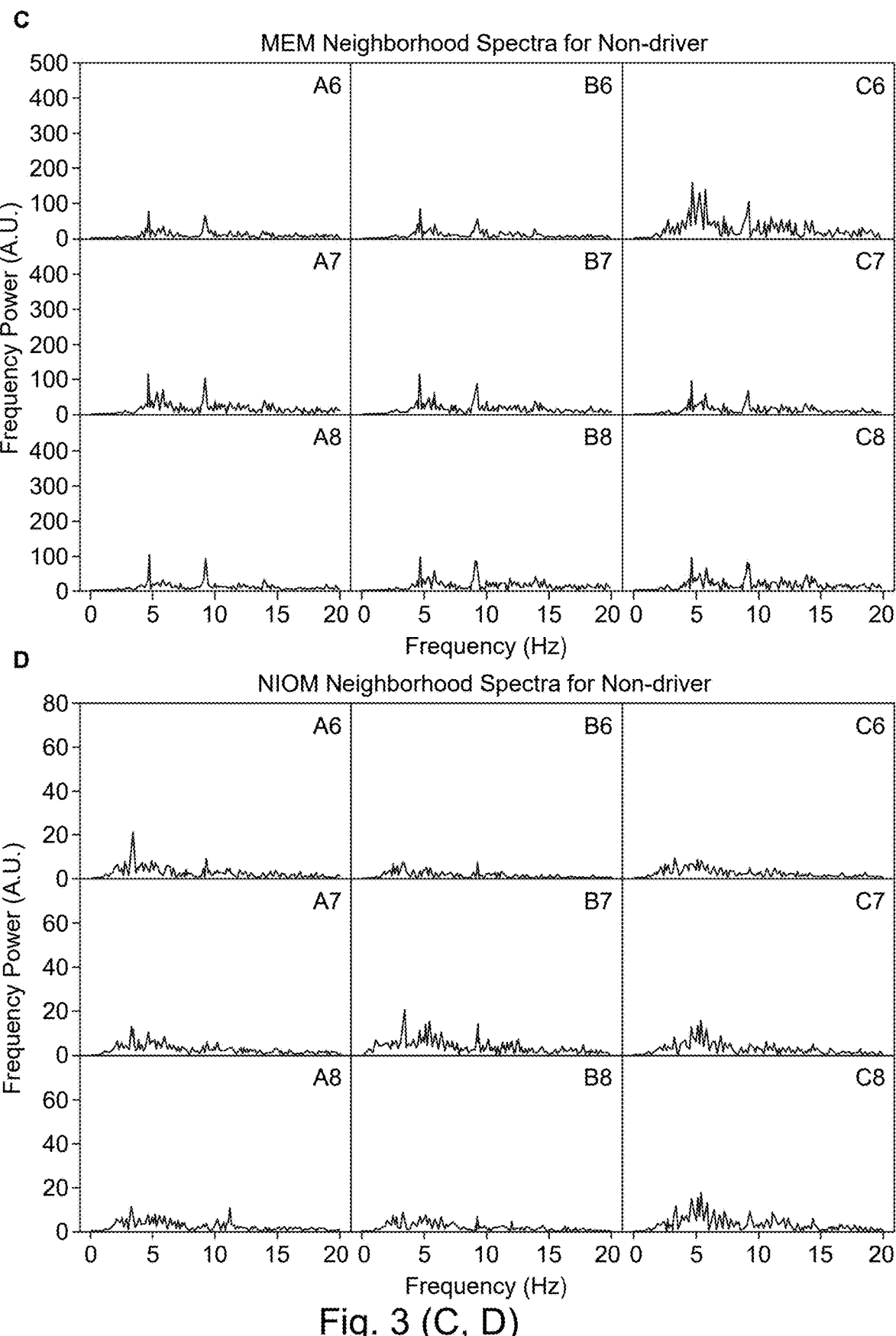
Fig. 3 (C, D)

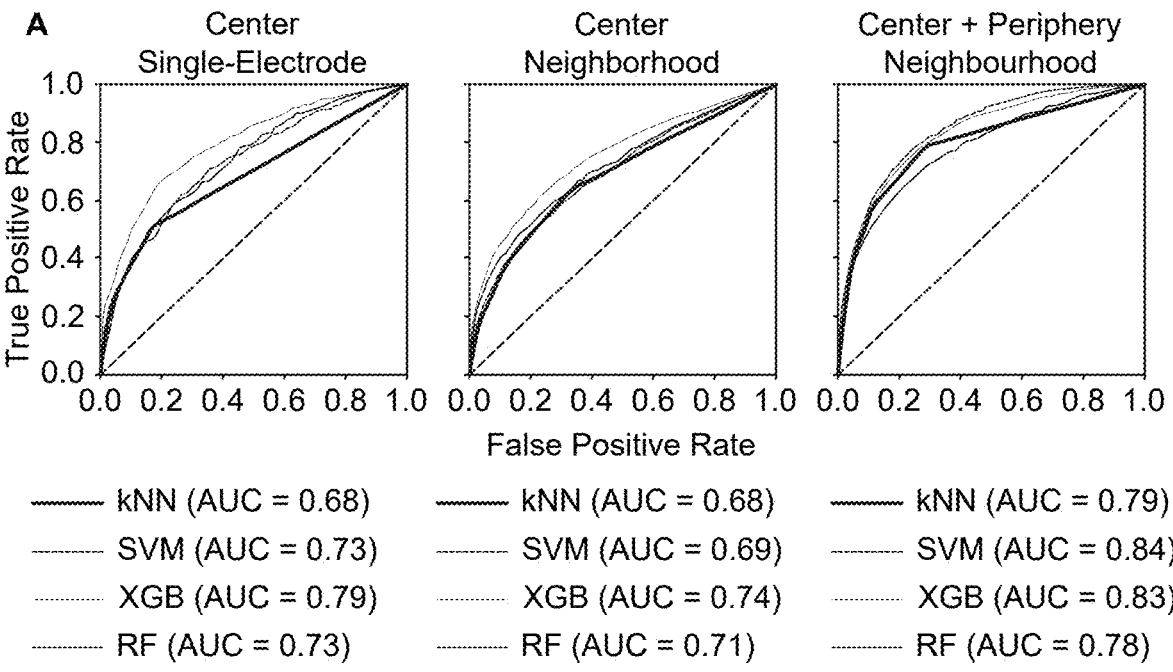
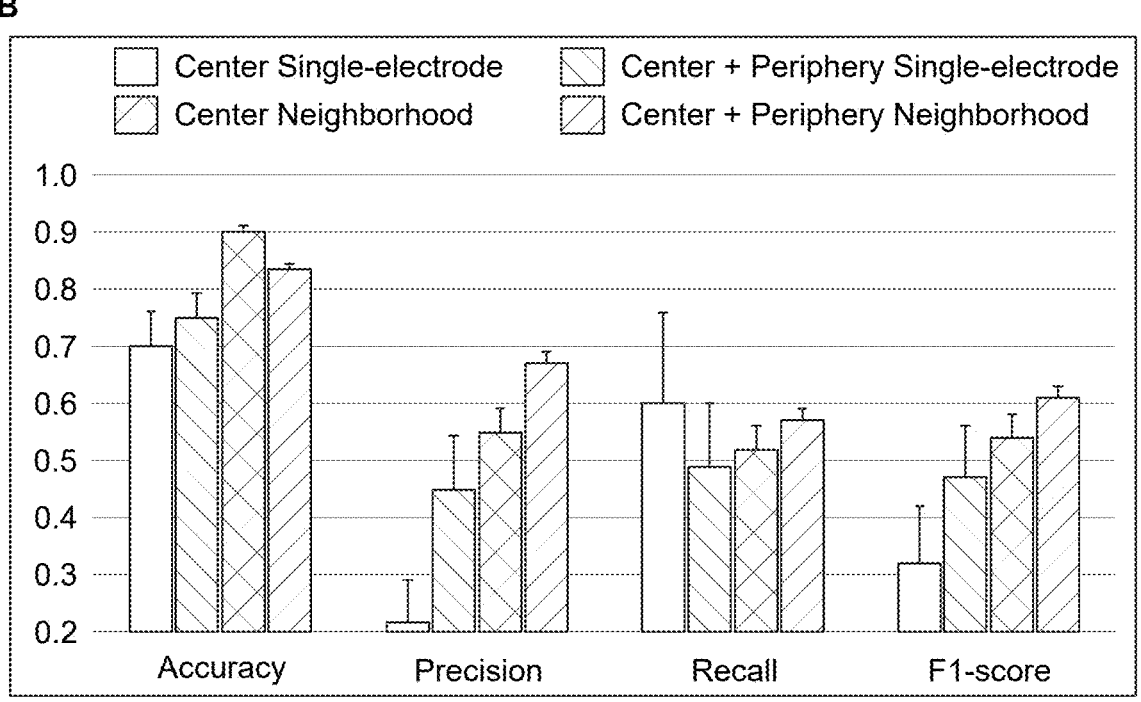
Fig. 6

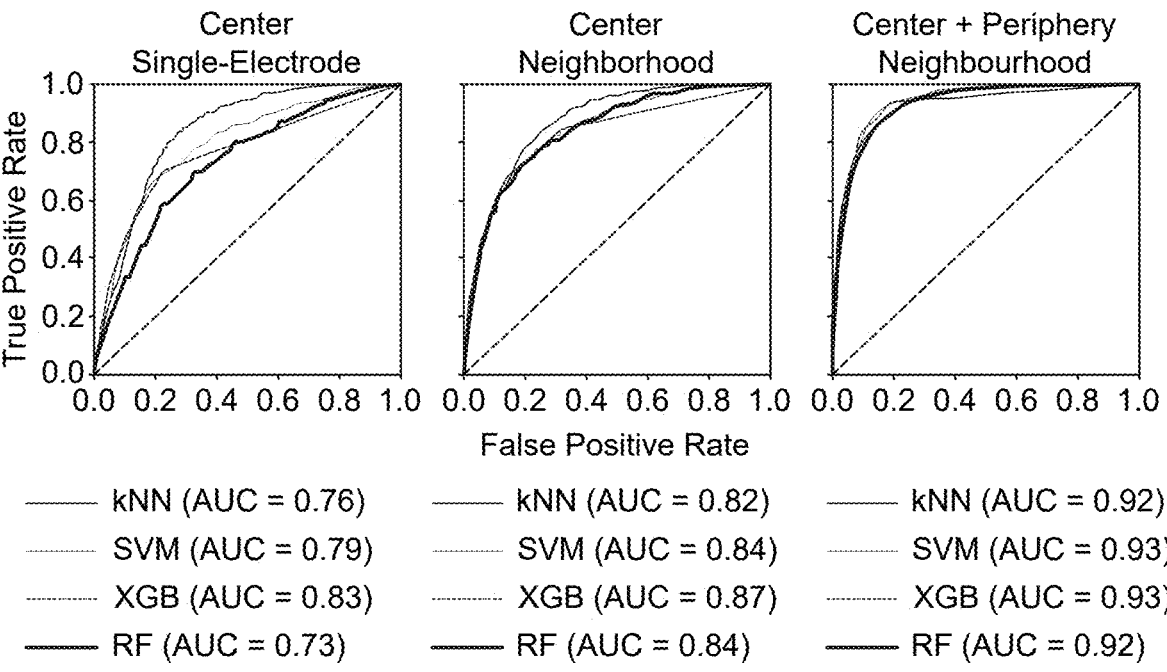
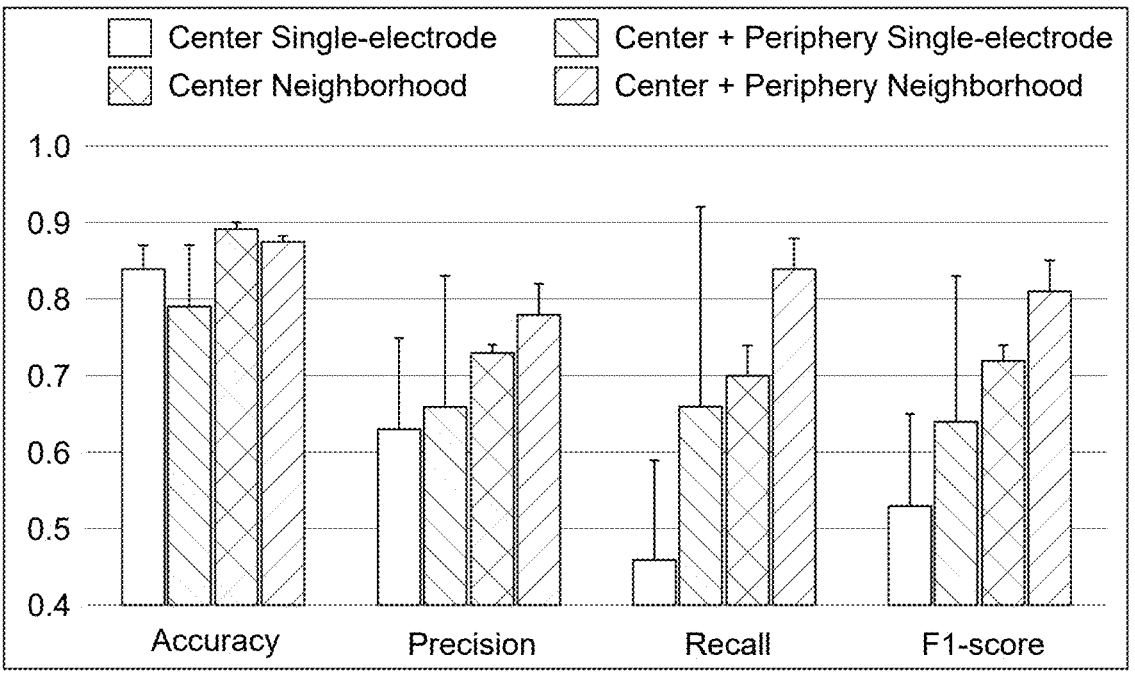
Fig. 8A

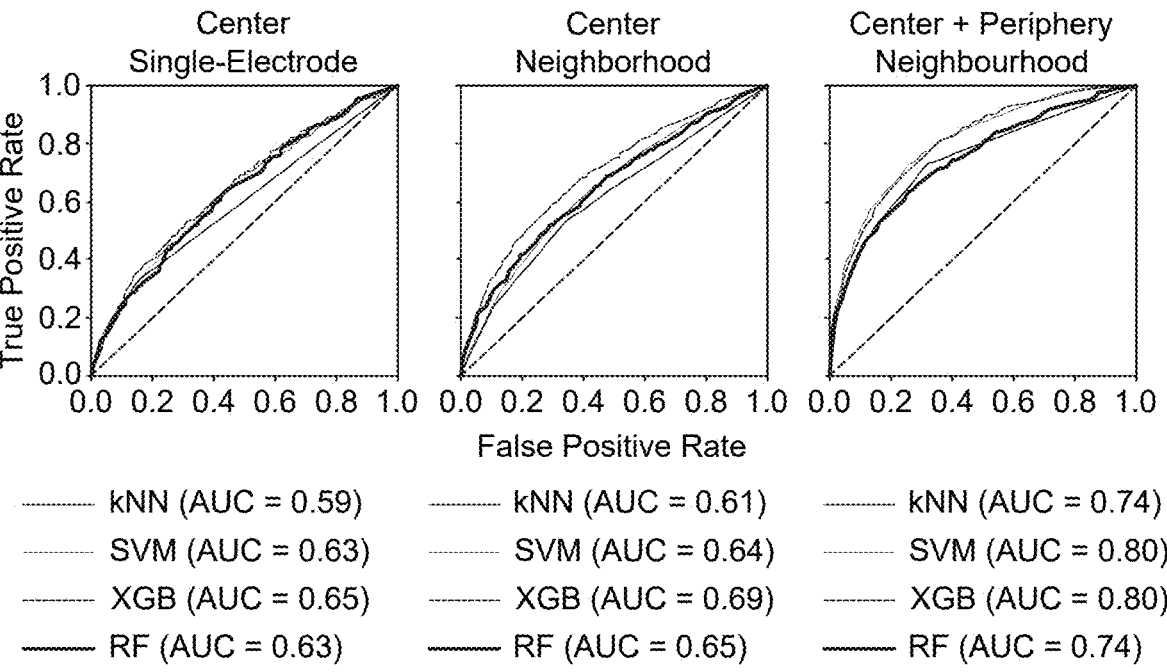
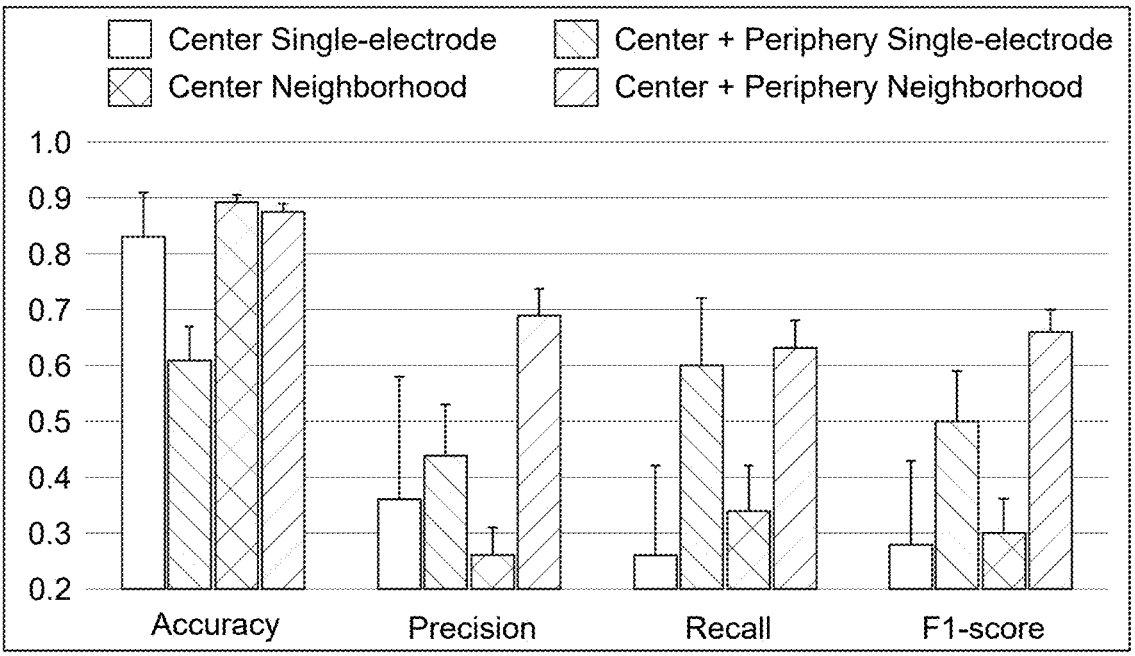
Fig. 8B

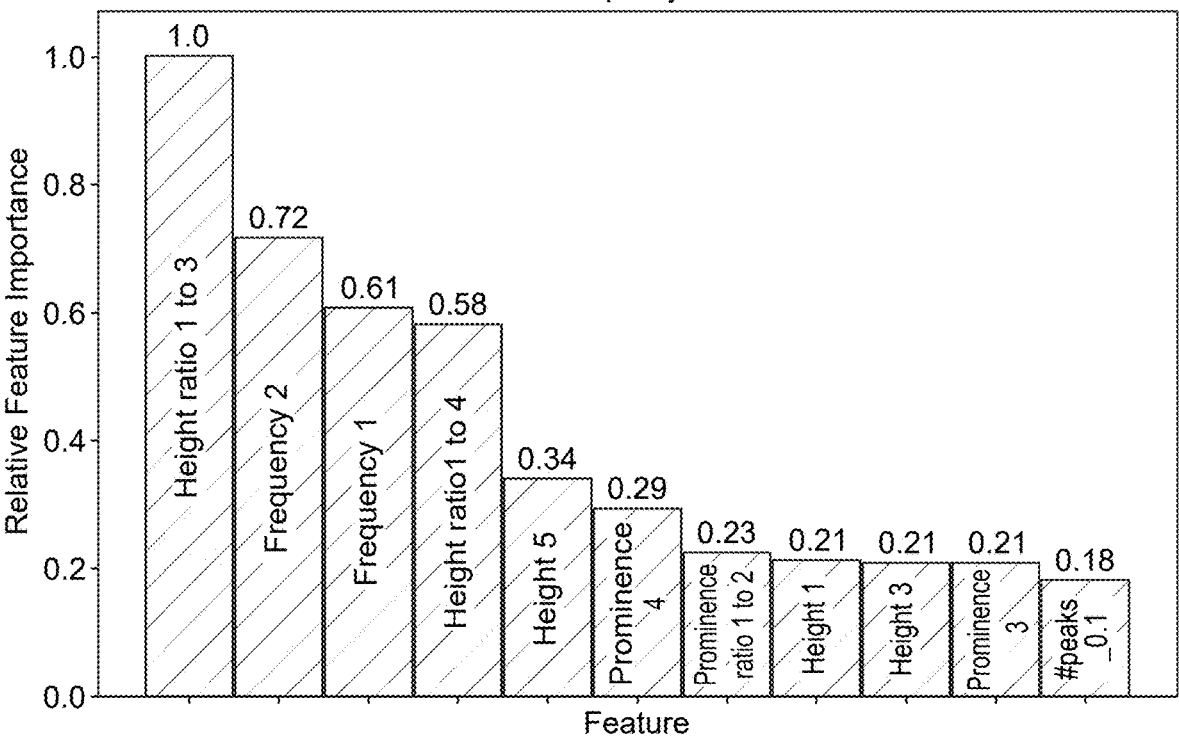
The Most Valuable Features for
AF HD Center+Periphery MEM Feature Set
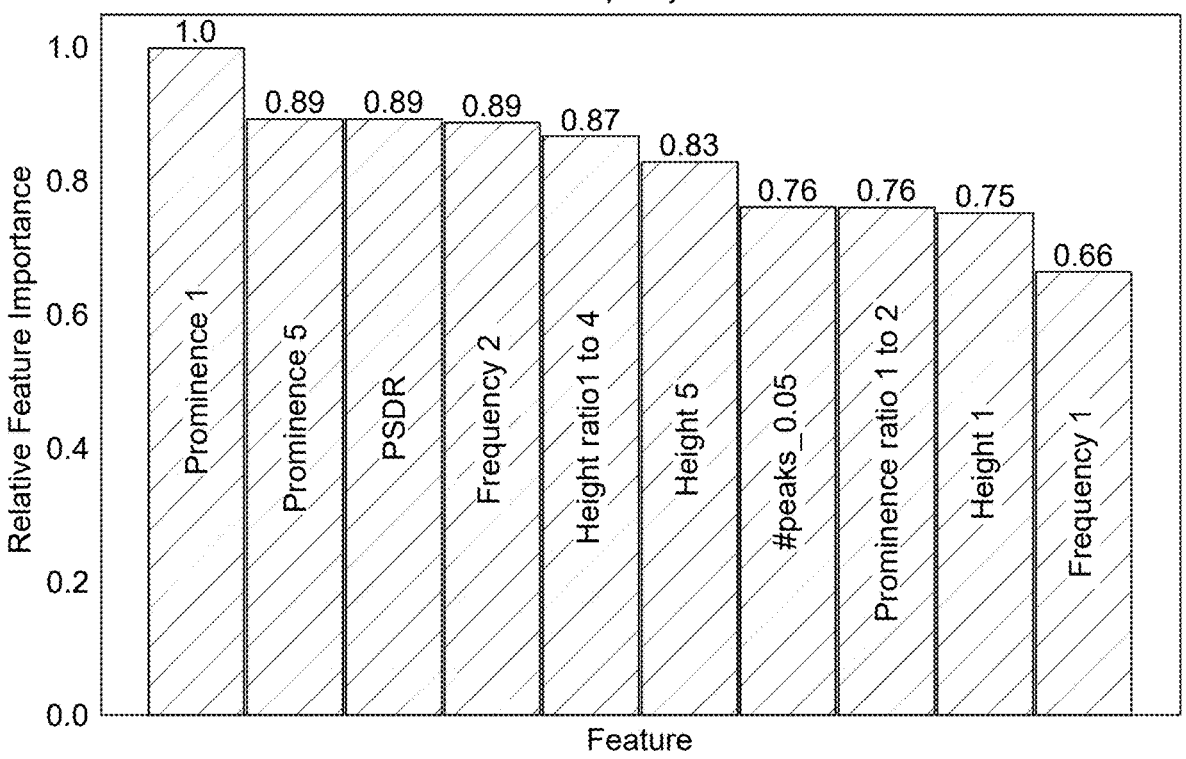
The Most Valuable Features for
AF LD Center+Periphery MEM Feature Set
Fig. 10

ARTIFICIAL INTELLIGENCE TRAINED WITH OPTICAL MAPPING TO IMPROVE DETECTION OF CARDIAC ARRHYTHMIA SOURCES

CROSS-REFERENCE TO RELATED APPLICATIONS

This application is a national stage application filed under 35 U.S.C. § 371 of PCT/RU2020/050089 filed May 6, 2020, which claims benefit of priority to U.S. Provisional Patent Application No. 62/843,800, filed May 6, 2019, the content of which is herein incorporated by reference in its entirety for all purposes.

BACKGROUND

Cardiac arrhythmias affect millions of people worldwide and are a significant cause of mortality and morbidity and create a significant strain on the healthcare system. Tachycardias, arrhythmias in which the heart beats too fast or in a disorganized manner, have been found to be sustained by one or more sources of electrical excitation located within pathologic regions of the heart. Some of the tachycardias that have been proposed to be maintained by an arrhythmic source include atrial fibrillation, atrial flutter, atrial tachycardia, ventricular tachycardia, and ventricular fibrillation. Atrial fibrillation (AF) is the most common cardiac arrhythmia and the leading cause of stroke in the world. The mechanism of this disease remains unclear, but several experimental and clinical studies suggest that AF may be caused and maintained by spatially-stable, extra-pulmonary sources of repetitive rotational activity called reentrant AF drivers. Promising treatment of these arrhythmias has been shown through the use of targeted ablation at the site of these sources to disrupt their pathologic function. However, locating these sources of arrhythmias and the optimal location to apply ablation lesions has hindered the success rates of these treatments. Current clinical electrode approaches (Ref. 1) including multi-electrode mapping (MEM) can record only the electrical signals from the surface and may not detect the transmural conduction within the 3-dimensional structure of the human atria. (Ref. 2) One potential solution to improve AF treatment is related to widespread adoption of Artificial Intelligence (AI) techniques. In particular, several studies have applied machine and deep learning algorithms to classify ECG recordings into sinus rhythm, AF, and other arrhythmias (Ref. 3,4). AI has been used to identify paroxysmal AF patients based on their sinus rhythm ECG (Ref. 5). AI was also used to identify the location of computationally simulated reentrant AF drivers in-silico (Ref. 6); however, many limitations have prevented translation of this work. Paramount among these limitations is the lack of a gold standard for AF driver detection in the clinical setting as clinical MEM is plagued by both false positives and false negatives (Ref. 7). Without a gold standard for validation, it would be impossible to correctly annotate the AI training set. Thus, an urgent need exists to develop validated AI algorithms to improve detection of cardiac arrhythmia sources in a patient. This includes determining a location of an AF driver that can be used during following operational intervention, such as patient-specific AF ablation.

SUMMARY

Embodiments disclosed herein relate to methods, systems and products for determining cardiac arrhythmia sources in a patient. This includes determining a location of cardiac arrhythmia, including atrial fibrillation (AF) sources or drivers in a patient's heart, and providing an ablation treatment plan.

In one embodiment, a computer-implemented method for determining a location of a source of cardiac arrhythmia in a patient's heart is provided, comprising at least the steps of: receiving electrogram signals acquired from a region of the patients' heart using a first set of electrodes; applying a pre-trained artificial intelligence (AI) model to predict the location of the cardiac arrhythmia source by using the received signals; wherein pre-training of the AI model comprises: (a) acquiring electrogram signals from explanted human hearts, said signals are generated by a second set of electrodes assembled into an electrode array that covers at least a part of the explanted human heart, and acquiring co-registered functional or structural imaging data in the part of the explanted human heart covered with the electrode array, wherein said functional and/or structural imaging data provide location of at least one source of cardiac arrhythmia; (b) processing said electrogram signals and functional and/or structural imaging data to learn characterizing features that will be used in the AI model; (c) assigning learned features characterizing electrogram signals generated from at least one electrode on the electrode array to corresponding features characterizing functional and/or structural imaging data generated adjacent to said at least one electrode; (d) classifying features characterizing electrogram signals generated from at least one electrode on the electrode array where functional and/or structural imaging data were acquired as corresponding to a source or to a non-source.

In another embodiment, in this computer-implemented method the source of cardiac arrhythmia is a driver of AF. Other cardiac rhythm disorders in which a source can be located and treated with ablation include atrial flutter, atrial tachycardia, ventricular fibrillation, ventricular tachycardia. The claimed methods are useful for determining location of a source of these arrhythmias.

In the present disclosure, an electrode array (or electrode grid) is an article that is used receive electrogram signals and may contain one or more electrodes.

In the present disclosure, a set of electrodes may contain one or more electrodes. In some embodiments, these electrodes may be assembled into electrode array (or electrode grid) that covers at least a part of a human heart.

In some embodiments, the AI model is an AI algorithm selected from the following group: any supervised machine learning binary and multiclass classification and regression algorithms (k-Nearest Neighbors model, Support Vector Machine model, Boosting algorithms, Logistic Regression, Random Forest etc.), neural networks (fully-connected neural networks, convolution neural networks, recurrent neural networks, etc.), or unsupervised (clustering, etc.) algorithms.

In some embodiments, pre-training of the AI model may be achieved utilizing functional data alone or structural data alone. In other embodiments, pre-training of the AI model may be achieved utilizing a combination of functional data and structural data.

During pre-training of the AI model, the characterizing features may be selected by a user, for example, for Machine Learning algorithms or may be automatically generated, for example, for neural networks or any unsupervised models.

In some embodiments, steps of pre-training of the AI model comprises: a) normalizing the recordings, applying band-pass filtering; b) (optional) data augmentation (windows of recordings); c) (optional) calculating Fourier transform or other transforms (wavelet etc.); d) (optional) generating features from transformed recordings; e) obtaining ground-truth labels for supervised learning.

In some embodiments, adjacent to at least one electrode on the electrode array means distance about 1 MM around said at least one electrode. In other embodiments, this distance may be 2 MM or 3 mm around said at least one electrode. In yet another embodiment, this distance may be 5 MM around said at least one electrode.

In some embodiments, assigning occurs for features that characterize electrogram signals generated around 3*3 or other kernels (matrix) of electrodes located on the electrode array.

In some embodiments, acquiring electrogram signals from explanted human hearts and acquiring co-registered functional and/or structural imaging data in the part of the explanted human heart means that electrogram signals and functional and/or structural imaging data are acquiring simultaneously.

In some embodiments, processing of electrogram signals and functional and/or structural imaging data may comprise generating Fourier transformed electrogram signals and Fourier transformed imaging signals, normalizing signals, band-pass filtering of signals, generating Hilbert transforms and other wavelet transforms of signals, and so on. Further, processing may comprise data augmentation (windows of recordings), and obtaining ground-truth labels for supervised learning models.

Examples of functional imaging data comprise, but are not limited to, optical mapping with voltage sensitive dyes (conventional dye, red-shifted near infrared dye), with calcium sensitive dyes, fluorescent proteins, organic dyes, and genetically encoded calcium and voltage sensors. Voltage sensitive dyes are known in the art and include, for example, di-4-ANBDQBS or any red-shifted dye, di-4-ANEPPS, di-8-ANEPPS, RH237. Examples of calcium sensitive dyes are also known (Rhod-2 and others) (Ref. 8-10).

Examples of structural imaging data comprise, without limitation, performing Magnetic resonance imaging (with and without addition of contrast agent, and delayed contrast scans), x-ray computed tomography (with and without addition of contrast agent), optical computed tomography, ultrasound imaging (extracorporeal, transesophageal, intracardiac).

Electrode assemblies disclosed here include any collection of electrodes or single electrode (catheter based or not) that is connected to an amplifier and a recording device. These electrode assemblies include any electrode and recording device combinations currently available on the market as well was electrode assemblies designed for the experimental setting. If assembly includes multiple electrodes, then the electrodes could be arranged in any geometry with any amount of space between electrodes. During pre-training on explanted human hearts both clinical and experimental electrode assemblies could be used; during diagnostics procedure electrodes designed for clinical use will preferably be used.

Some embodiments of the invention comprise a method for providing a cardiac arrhythmia ablation treatment plan, the method comprising: receiving electrogram signals acquired from a region of the patients' heart using a first set of electrodes;

applying a pre-trained artificial intelligence (AI) model to predict the location of the cardiac arrhythmia source by using the received signals; wherein pre-training of the AI model comprises: (a) acquiring electrogram signals from explanted human hearts, said signals are generated by a second set of electrodes assembled into an electrode array that covers at least a part of the explanted human heart, and acquiring co-registered functional and/or structural imaging data in the part of the explanted human heart covered with the electrode array, wherein said functional and/or structural imaging data provide location of at least one source of cardiac arrhythmia;

(b) processing said electrogram signals and functional and/or structural imaging data to learn characterizing features that will be used in the AI model; (c) assigning learned features characterizing electrogram signals generated from at least one electrode on the electrode array to corresponding features characterizing functional and/or structural imaging data generated adjacent to said at least one electrode; (d) classifying features characterizing electrogram signals generated from at least one electrode on the electrode array where functional and/or structural imaging data were acquired as corresponding to a source or to a non-source; (e) providing a cardiac arrhythmia ablation treatment plan that includes an ablation of the located source as at least a portion of said cardiac arrhythmia treatment plan.

Some embodiments of the invention also comprise a system for determining a location of a source of arrhythmia in a patient's heart, the system comprising: at least one computing device comprising at least one non-transitory computer readable storage medium configured to store instructions executable by at least one processor for determining the source location in the patient's heart, the computing device being configured to: (a) receive electrogram signals acquired from a region of the patients' heart using a first set of electrodes; (b) apply a pre-trained artificial intelligence (AI) model to predict the location of the cardiac arrhythmia source by using the received signals; wherein pre-training of the AI model comprises: acquiring electrogram signals from explanted human hearts, said signals are generated by a second set of electrodes assembled into an electrode array that covers at least a part of the explanted human heart, and acquiring co-registered functional and/or structural imaging data in the part of the explanted human heart covered with the electrode array, wherein said functional and/or structural imaging data provide location of at least one source of cardiac arrhythmia; processing said electrogram signals and functional and/or structural imaging data to learn characterizing features that will be used in the AI model; assigning learned features characterizing electrogram signals generated from at least one electrode on the electrode array to corresponding features characterizing functional and/or structural imaging data generated adjacent to said at least one electrode; classifying features characterizing electrogram signals generated from at least one electrode on the electrode array where functional and/or structural imaging data were acquired as corresponding to a source or to a non-source.

In some preferred embodiments, the disclosed system may comprise means for collecting electrogram signals and cardiac structural imaging data, processing acquired signals and integrating signals from multiple data sets, running artificial intelligence prediction algorithm, and displaying results to a clinical operator for treatment planning. Electrogram signals can be recorded from regions of the patient's heart through use of any commercially available electrode catheter, such as the FIRMap and HD Grid catheters from Abbott EP, and the PentaRay or Lasso catheters from Biosense Webster, Acutus non-contact catheter, and Rhytmia HDx Boston Scientific. Electrogram signals can also come from body surface recording systems such as the Cardioinsight Electrocardiographic Imaging Vest. The electrogram signals are then run through an amplifier, with preferred embodiments using multi-channel amplifiers such as the EnSite Amplifier from Abbott EP. The signals from the amplifier are then run into a computing system. The computing system can co-register the electrogram signals with the specific region of the patient's heart from which they were recorded, with preferred embodiments comprising magnetic or impedence based electroanatomical mapping systems such as CARTO from Biosense Webster or Ensite Precision from Abbott EP.

In other embodiments, a computing system will be able to integrate cardiac structural imaging data, such as MRI or CT scans, loaded onto the system through an external hard drive or downloaded from a cloud-based data storage application. The system will also include a display that can be used by a clinical operator to aid in the planning of cardiac arrhythmia ablation treatments. In a preferred embodiment, the display will feature a 2D or 3D rendition of the patient's heart with each region color-coded or marked in some way based on the predicted probability of each region to be a cardiac arrhythmia source.

In some other embodiments, the disclosed system may comprise a system for the integrated collection of cardiac structural imaging data obtained with MRI or CT; the system is able to process acquired imaging data and integrate signals from the data sets, run an artificial intelligence prediction algorithm, and display results to a clinical operator for treatment planning. Some embodiments of the invention also comprise a non-transitory computer-readable medium comprising computer-executable code for providing a cardiac arrhythmia ablation treatment plan, said computer-executable code comprising instructions that, when executed by a computer, causes the computer to: (a) receive electrogram signals acquired from a region of the patients' heart using a first set of electrodes; (b) apply pre-trained artificial intelligence (AI) model to predict the location of the cardiac arrhythmia source by using the received signals; wherein pre-training of the AI model comprises: acquiring electrogram signals from explanted human hearts, said signals are generated by a second set of electrodes assembled into an electrode array that covers at least a part of the explanted human heart, and acquiring co-registered functional and/or structural imaging data in the part of the explanted human heart covered with the electrode array, wherein said functional and/or structural imaging data provide location of at least one source of cardiac arrhythmia; processing said electrogram signals and functional and/or structural imaging data to learn characterizing features that will be used in the AI model; assigning learned features characterizing electrogram signals generated from at least one electrode on the electrode array to corresponding features characterizing functional and/or structural imaging data generated adjacent to said at least one electrode; classifying features characterizing electrogram signals generated from at least one electrode on the electrode array where functional and/or structural imaging data were acquired as corresponding to a source or to a non-source; provide an cardiac arrhythmia ablation treatment plan that includes the located source ablation as at least a portion of said cardiac arrhythmia treatment plan.

After identification of the source of cardiac arrhythmia, ablation (radiofrequency, cryoablation, laser, radiosurgery, etc.) lesion sets may be delivered through the same catheter, a separate catheter, or a separate system can be planned based on the source location. Ablation lesion sets may be organized as a single lesion, a cluster of lesions, or linear lesions. Ablation lesions may be placed at the location of the source and/or include adjacent tissue. Ablation lesion sets may be connected continuously to unexcitable tissue, such as an anatomical border, scar, or prior lesion set. One embodiment of an ablation method and device is disclosed in U.S. Pat. No. 5,383,917, the entirety of which is hereby incorporated by reference herein.

Features from any of the disclosed embodiments can be used in combination with one another, without limitation. In addition, other features and advantages of the present disclosure will become apparent to those of ordinary skill in the art through consideration of the following detailed description and the accompanying drawings.

BRIEF DESCRIPTION OF DRAWINGS

The detailed description is set forth with reference to the accompanying Figures.

FIG. 3 (A)—Representative Fourier spectra from driver electrodes; (B)—Representative Fourier spectra from driver optical action potentials; (C)—Representative Fourier spectra from non-driver electrodes; (D)—Representative Fourier spectra from non-driver optical action potentials. A.U.=arbitrary units, MEM=multi-electrode mapping, NIOM=near-infrared optical mapping.

FIG. 4—3D myofiber tracts of the intact human atria show misalignment in AF driver regions displayed from the PLA (A) and LRA (B) views. Right, Fibrosis tends to deposit along the myofiber orientations to enhance structural and electrical anisotropy. AF—atrial fibrillation, PMs—pectinate muscles, CT—crista terminalis, IAS—interatrial septum, IVC/SVC—inferior/superior vena cava, LA/RA—left/right atrium, LAA/RAA—left/right atrial appendage, LS/LI/RS/RI PV—left superior/left inferior/right superior/right inferior pulmonary vein, LRA—lateral right atrium, PLA—posterior left atrium. Used with permission from Zhao et al (Ref. 11).

FIG. 6 (A)—The Receiver Operating Characteristic (ROC) curves for different feature sets of AF dataset as analyzed by 4 algorithms. (B)—Performance metrics of kNN binary classification into AF reentrant driver vs non-driver recordings for different feature sets. Asterisk shows the significant difference between any two metrics within the group by ANOVA. MEM=Multi-Electrode Mapping, NIOM=Near-Infrared Optical Mapping. AUC=Area Under the Curve, kNN=k-Nearest Neighbors, SVM=Support Vector Machine, RF=Random Forest, XGB=XGBoost Classifier.

FIG. 8 (A)—The ROC curves for different feature sets of AF HD dataset as analyzed by 4 algorithms. Below, performance metrics of binary classification into AF reentrant driver vs non-driver recordings from AF HD dataset for different feature sets. Asterisk shows the significant difference between any two metrics within group of three. (B)—The ROC curves for different feature sets of AF HD dataset as analyzed by 4 algorithms. Below, performance metrics of binary classification into AF reentrant driver vs non-driver recordings from AF LD dataset for different feature sets. Asterisk shows the significant difference between any two metrics within the group by ANOVA. Abbreviations as in FIG. 5, LD=Lower-Density catheter, HD=Higher-Density catheter.

FIG. 10—Names and relative feature importance of top valuable features for neighbor-electrodes MEM feature set for the samples from high-density catheter (AF HD, top Panel) and from low-density catheter (AF LD, bottom Panel). Abbreviations as in FIG. 3. PSDR—Peak to Standard Deviation Ratio.

DETAILED DESCRIPTION OF THE INVENTION

Figure 1A:
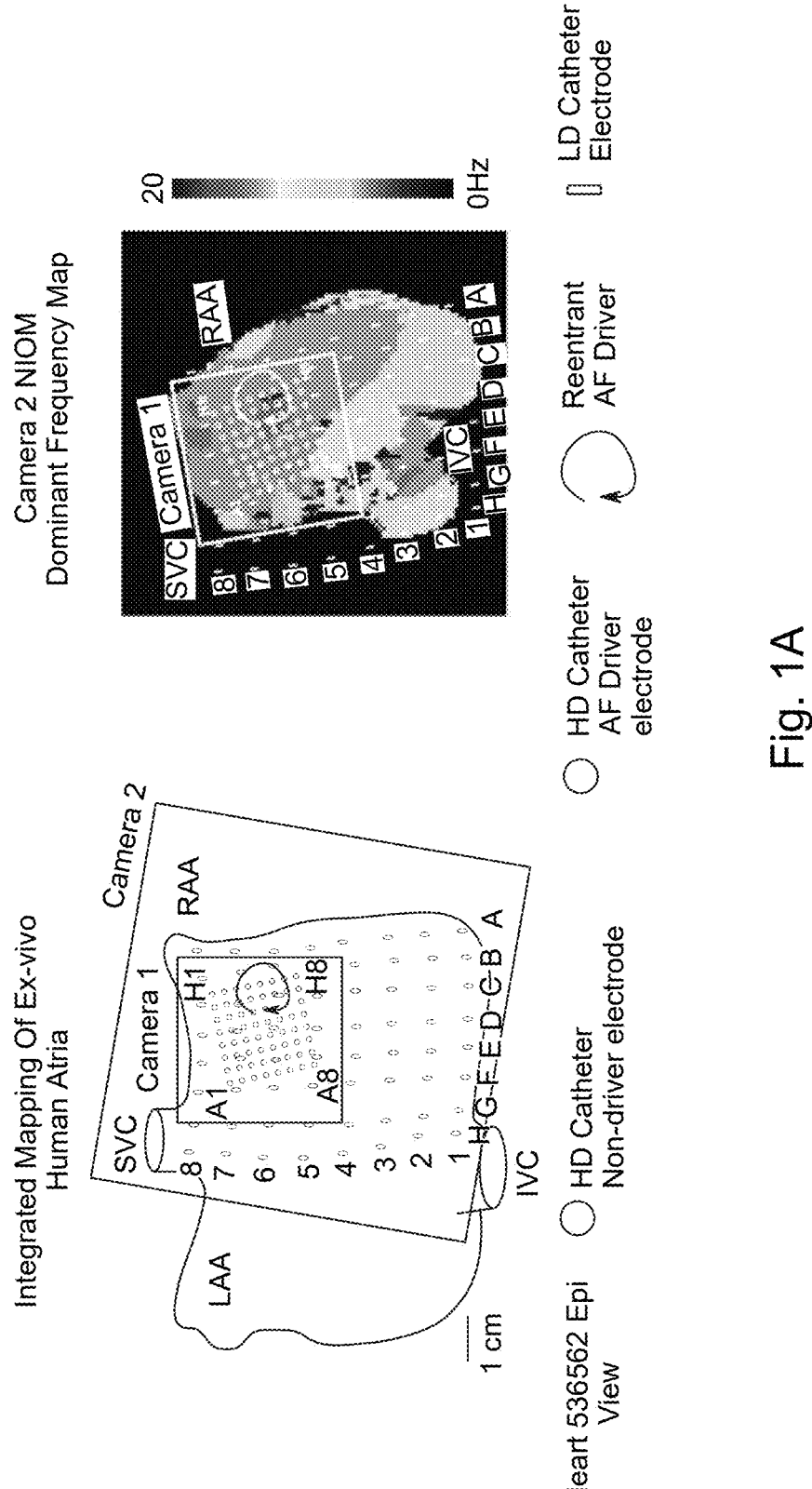
FIG. 1. (A)—Example of a sustained AF episode maintained by reentrant driver, which was recorded simultaneously by clinical MEM (Higher-Density (HD) and Lower-Density (LD) catheters) and high-resolution NIOM (Cameras 1-2). (B)—Ground-truth labels for electrodes (light gray—center of driver, black—non-driver) were acquired by NIOM, driver periphery labels (light gray/black) were counted as driver in center plus periphery annotation or as non-driver in driver center annotation. (C)—Fourier spectra of annotated MEM electrograms and co-located NIOM OAPs were used for generation of frequency features for Machine Learning approach. LAA/RAA=Left/Right Atria Appendage, I/SVC=Inferior/Superior Vena Cava, MEM=Multi-Electrode Mapping, NIOM=Near-Infrared Optical Mapping, OAP=Optical Action Potential, A.U.=Arbitrary Units.

In this description, the terms "includes" and "including" are deemed as meaning "includes, among other things". These terms are not intended to be interpreted as "consists only of". Unless otherwise specified, the technical and scientific terms in this description have standard meanings, generally accepted in the scientific and technical literature. References (1-25) are included below to provide more information about some aspects of the invention. The contents of these references are incorporated into this description.

Disclosed herein are methods and products configured to detect location of a source of cardiac arrhythmia in a patient's heart. In the following description, for the purposes of explanation, numerous specific details are set forth in order to provide a thorough understanding of example embodiments or aspects. It will be evident, however, to one skilled in the art that an example embodiment may be practiced without necessarily using all of the disclosed specific details. Moreover, in the following description, atrial fibrillation is used as an example of a cardiac arrhythmia maintained by a source. Atrial fibrillation can be replaced with any of the other cardiac arrhythmias known to be maintained by sources, such as atrial tachycardia, atrial flutter, ventricular tachycardia, and ventricular fibrillation.

Atrial fibrillation (AF) can be maintained by localized sources or drivers. However, AF driver detection by clinical surface-only multi-electrode mapping (MEM) has relied on subjective interpretation of activation maps and movies, such as with the RhythmView® system. The inventors have shown that these limitations in the visualization of reentrant AF drivers can be overcome in the ex-vivo, or explanted, human heart by utilizing functional and/or structural imaging data, such as high-resolution subsurface near-infrared optical mapping (NIOM) with submillimeter resolutions (Ref. 11-14), and the methods disclosed in these papers are incorporated herein. Disclosed further herein are methods and products aimed to increase accuracy of AF driver detection in a clinical setting based on an artificial intelligence (AI) model pre-trained with uniquely obtained sets of data. It will be evident from the following data that application of AI, validated by functional and/or structural imaging data, to electrogram spectra may accurately automate driver detection by a standard multi-electrode mapping. To fully understand how the AI model can be trained and implemented in a diagnostic environment, this disclosure will describe the invention in the context of classifying MEM and NIOM data simultaneously obtained from explanted human atria by way of examples.

Example 1. Explanted Human Hearts and Inclusion Criteria

Deidentified, coded human hearts were obtained from The Ohio State University Cardiac Transplant team and LifeLine of Ohio in accordance with The Ohio State University Institutional Review Board. The human hearts are received from the Ohio State Cardiac Transplant team and the local organ procurement organization LifeLine of Ohio (with and without arrhythmia history and comorbidities including heart failure, hypertension, diabetes). In this embodiment, only atrial preparations with sustained AF (>1 min) and localized drivers confirmed by NIOM were included in the study's driver analysis (n=11).

Explanted hearts were cardioplegically-arrested and cooled to 4° C. in the operating room during transport, dissection, and cannulation. Intact human biatrial preparations were isolated, coronary-perfused and superfused with 36.5±0.5° C. oxygenated Tyrode's solution under constantly maintained pH (7.35±0.05) and pressure (55±5 mmHg), immobilized with pre-warmed and filtered 10 μM blebbistatin (Abcam), and stained with pre-warmed and filtered near-infrared voltage sensitive dye di-4-ANBDQBS (10-40 μM, University of Connecticut) (Ref. 11,13,17). Preparations were then equilibrated for 20 to 30 minutes before any recordings. All preparations excluded regions of poor coronary perfusion/ischemia consequently poorly perfused tissue was trimmed and arterial leaks were ligated with silk sutures. Trimmed areas were limited and located adjacent to the surgical cut, which never interfered with atrial arterial supply or the viability of tissue for optical mapping. Optical activation times for each pixel were marked at the maximum positive derivative of the optical action potential upstroke or using 50% of the OAP amplitude (AP50%). The above example details one embodiment of the invention. Other embodiments may include the above and any combination of the following alternatives. Explanted hearts can come from human donors as well as commonly used research animal models, such as canine, porcine, oovine, caprine, lapine, or rodent. Explanted hearts can include the whole heart, as in commonly used Langendorff perfusion approaches (Ref. 10) or any portion of the heart still viable by perfusion or superfusion, as in isolated whole atrial preparations (Ref. 15) or partial atrial (Ref. 12) or partial ventricular preparations (Ref. 16).

Example 2. Optical Mapping of Coronary-Perfused Human Atria to Define AF Driver Regions The authors employed high-resolution near-infrared subsurface optical mapping (NIOM), the only approach currently able to reveal subsurface conduction in human atria up to 4 mm and thus detect intramural AF driver activation as previously described (Ref. 12,14,15). Human atria (n=11) were isolated, coronary-perfused, immobilized with blebbistatin (10 µM, Abcam), and stained with near-infrared voltage sensitive dye, di-4-ANBDQBS (10-40 µM, University of Connecticut Health Center). Preparations were then equilibrated for 20 to 30 minutes before any recordings. All preparations excluded regions of poor coronary perfusion/ischemia consequently poorly perfused tissue was trimmed and arterial leaks were ligated with silk sutures. Trimmed areas were limited and located adjacent to the surgical cut, which never interfered with atrial arterial supply or the viability of tissue for optical mapping. Optical activation times for each pixel were marked at the maximum positive derivative of the optical action potential upstroke or using 50% of the OAP amplitude (AP50%) (Ref. 12,14).

Ex-vivo panoramic and transmural NIOM employed three to four CMOS cameras (spatial resolution 0.3-1.1 mm, 1000 fps, MiCAM Ultima-L, SciMedia Ltd, CA), as previously described (Ref. 12,13). Biatrial (n=6) and lateral right atrium (n=5) NIOM was conducted during sustained AF episodes to identify AF drivers as the ground truth with a customized Matlab program (Ref. 12).

Induction of sustained AF by burst pacing was attempted in all hearts at baseline conditions in the absence of all pharmacologic stimulation. If AF was uninducible or spontaneously terminated, AF induction was then tested during consistent perfusion of mild pharmacologic challenge, as previously described (Ref. 12,14,15) to represent autonomic tone or metabolic stress experienced by AF patients. Atria in which AF could not be sustained during mild pharmacologic challenge were excluded from the study.

The above example details one embodiment of the invention. Other embodiments may include the above and any combination of the following alternatives. Functional signals can be acquired from optical mapping with other voltage sensitive dyes (conventional dye, red-shifted near infrared dye), with calcium sensitive dyes, and fluorescent proteins. Voltage sensitive dyes are known in the art and include, for example, di-4-ANBDQBS or any red-shifted dye, di-4-ANEPPS, di-8-ANEPPS, or RH237. Optical mapping can also be performed through the use of other fluorescent proteins, organic dyes, and genetically encoded calcium and voltage sensors (Ref. 8-10). Examples of calcium sensitive dyes are also known, such as Rhod-2. Optical mapping can also be done through the use of different camera set ups with one or more cameras (Ref. 12,15)

including photodiode arrays (PDA), charge coupled device (CCD) and Complementary Metal Oxide Semiconductor (CMOS) (Ref. 8-10).

Example 3. Electrode Mapping Electrograms

Figure 1B:
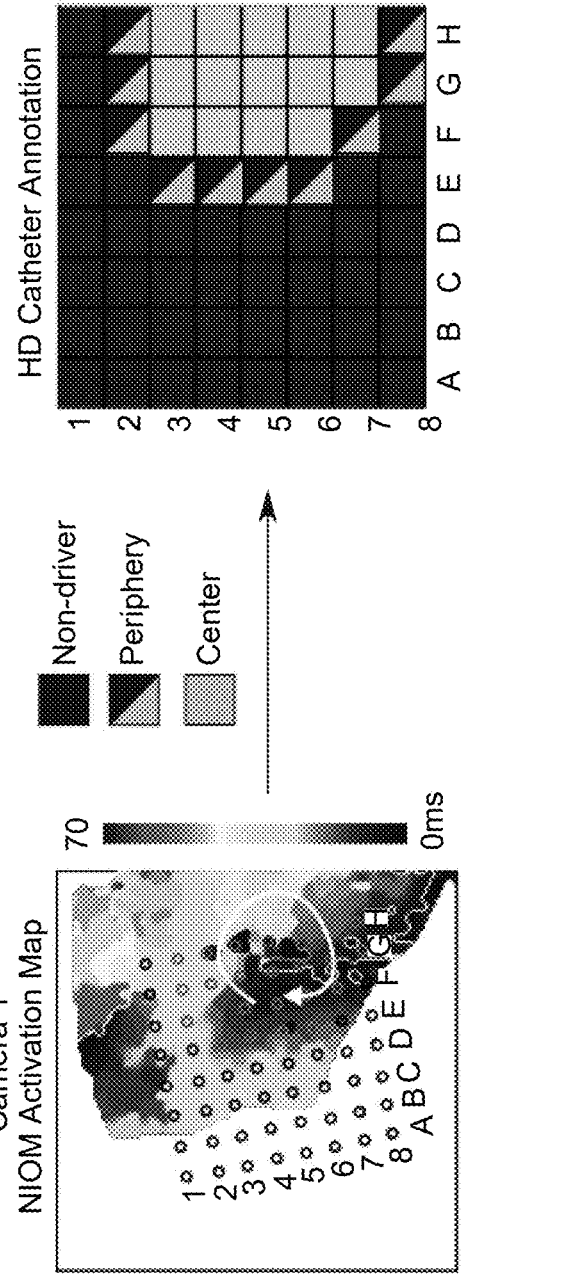
Figure 1C:
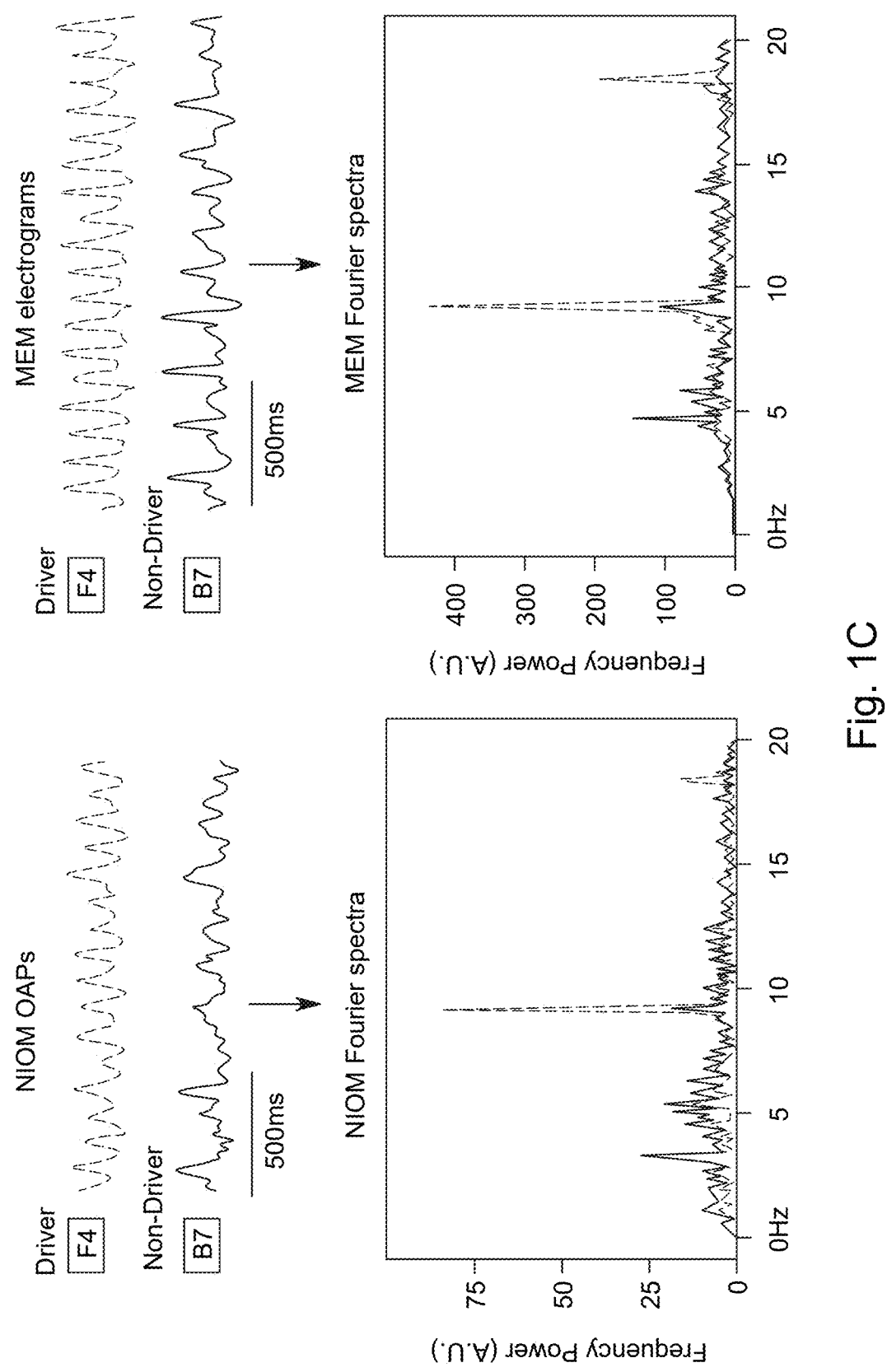

For simultaneous NIOM and clinically-relevant MEM, two types of 64-electrode (8×8) catheter grids were used. The Lower Density [LD] electrode array (Ref. 13) had inter-electrode distance 9 mm, ~70×72 mm surface coverage, and approximated clinically used moderate resolution basket catheters. The Higher Density [HD] electrode array (Ref. 8) had inter-electrode distance 3 mm, 24×24 mm surface coverage. The catheter array was placed on the atrial tissue to cover the driver region indicated by the NIOM activation map (FIG. 1). Each recording was taken with the electrodes in a single position and point-by-point mapping was not used. Electrograms were recorded during the AF episodes using either LD (n=25) or HD (n=7) catheters simultaneously with NIOM optical action potentials (OAPs). The duration of the recordings varied from 8 to 16 seconds, as limited by high-resolution four cameras NIOM recording system.

The above example details one embodiment of the invention. Other embodiments may include the above and any combination of the following alternatives. Electrograms recorded in the ex-vivo setting can come from any commercially available electrode catheter, such as the FIRMap and HD Grid catheters from Abbot EP and the PentaRay or Lasso catheters from Biosense Webster, Acutus non-contact catheter, and Rhytmia HDx Boston Scientific, Electrograms can also be recorded from experimental electrode arrays. The term electrode array used throughout this application refers to a device containing one or more electrodes. Electrode arrays can contain electrodes within any geometry with any inter-electrode space. Electrograms recorded for the training set can include unipolar and bipolar signals. Electrograms can be recorded from contact, non-contact electrodes, and body surface electrodes (Ref. 2). Electrode arrays used to record the training set electrograms can be the same or differ from the electrode arrays used in the clinical treatment plan. Electrograms used in the training set can come from a single region of the ex-vivo heart while the electrode array remains stationary or can be come from multiple regions of the ex-vivo heart as the electrode array is moved, as in sequential mapping known in the art (Ref. 17).

Example 4. Data Annotation Workflow

The ground truth for driver annotation was the same as in the previously published studies (Ref. 12,13). First, NIOM dominant frequency (DF, the frequency of the highest peak in the Fourier spectrum) was used to identify the fastest activating region, and then activation patterns based on the maximum derivative of NIOM OAPs are used to determined surface activation patterns within this region. It is known (Ref. 12,13) that intramural reentrant AF drivers could be identified at the surface with reentrant (>270° rotation), partial reentrant (>180° rotation), focal (centrifugal activation) patterns. The preferential conduction path of the AF drivers as seen by NIOM were used as the ground truth for electrode annotation. The preferential driver activation paths were defined independently by three reviewers and final reported annotation represents agreement among all three reviewers. Electrodes within one ablation lesion distance (~5 mm) of the paths were defined as driver center electrodes (class 1) and electrodes outside of this distance threshold were defined as non-driver (class 0). Furthermore, non-diagonal adjacent electrodes were defined as driver periphery electrodes and were considered non-driver (class 0) in "driver center dataset" and driver (class 1) in "driver center plus periphery dataset". (FIG. 1). Uninformative recordings (e.g., from electrodes with bad tissue contact) were annotated as outliers (class −1). Datasets were also labelled as in accordance with the catheter resolution (Table 1). Such break-down into independent datasets was meant to preserve the recordings' origin and to compare the impact of catheter resolution on reentrant AF driver differentiation. A simultaneously recorded NIOM OAP was manually selected within less than 1 mm adjacent to each electrode location. By doing so, the recordings from the optical and the electrode mapping modalities were guaranteed to be co-located for further correlation and AI-based analysis.

TABLE 1

Number of spectra from different datasets and modalities used for Examples. The percentage of center plus periphery drivers and uninformative electrodes indicated in parentheses, respectively.

| Dataset with Atrial Fibrillation (AF) | Lower-Density (LD) catheter | Higher-Density (HD) catheter | Combination |
|---|---|---|---|
| Number of MEM recordings | 1600 (17%, 8%) | 448 (27%, 9%) | 2048 (20%, 7%) |
| Number of MEM spectra | 17875 (19%, 0%) | 8919 (33%, 0%) | 26794 (23%, 0%) |
| Number of NIOM recordings | 602 (32%, 6%) | 448 (21%, 9%) | 1050 (30%, 4%) |
| Number of NIOM spectra | 6936 (34%, 0%) | 8919 (32%, 0%) | 15855 (33%, 0%) |
| Number of MEM + NIOM spectra | 6824 (34%, 0%) | 8919 (33%, 0%) | 15743 (33%, 0%) |

Example 5. Raw Signal Preprocessing

Signal normalization and 2-20 Hz Butterworth band-pass filtering were applied to all recordings. MEM and NIOM recordings were then resampled into 5 second segments by a sliding window with 0.5 second steps (for Short-Time Fourier Transformation) (Ref. 18,19). Fourier spectra were then calculated for each 5 second recording using a Fast Fourier Transform from NumPy library in Python (https://numpy.org/).

A set of frequency features for training an AI model was then generated (learned) from each Fourier spectrum, including DF listed as Frequency 1 among all other features in Table 2.

TABLE 2

List of features that will be included in a variant of supervised machine learning algorithm discussed in Example 8.

| # | Feature |
|---|---|
| 1 | #peaks_0.05 |
| 2 | #peaks_0.1 |
| 3-7 | frequency 1 -5 |
| 8-12 | height 1-5 |
| 13-17 | width 1-5 |
| 18-22 | prominence 1-5 |
| 23 | PSDR |
| 24 | height ratio between peaks 1 and 2 |
| 25 | height ratio between peaks 1 and 3 |

TABLE 2-continued

List of features that will be included in a variant of supervised machine learning algorithm discussed in Example 8.

| # | Feature |
|---|---|
| 26 | height ratio between peaks 1 and 4 |
| 27 | height ratio between peaks 2 and 3 |
| 28 | height ratio between peaks 2 and 4 |
| 29 | height ratio between peaks 3 and 4 |
| 30 | prominence ratio between peaks 1 and 2 |
| 31 | prominence ratio between peaks 1 and 3 |

TABLE 2-continued

List of features that will be included in a variant of supervised machine learning algorithm discussed in Example 8.

| # | Feature |
|---|---|
| 32 | prominence ratio between peaks 1 and 4 |
| 33 | prominence ratio between peaks 2 and 3 |
| 34 | prominence ratio between peaks 2 and 4 |
| 35 | prominence ratio between peaks 3 and 4 |

MEM = Multi-Electrode Mapping, PSDR-peak-to-standard deviation ratio.

Figure 2:
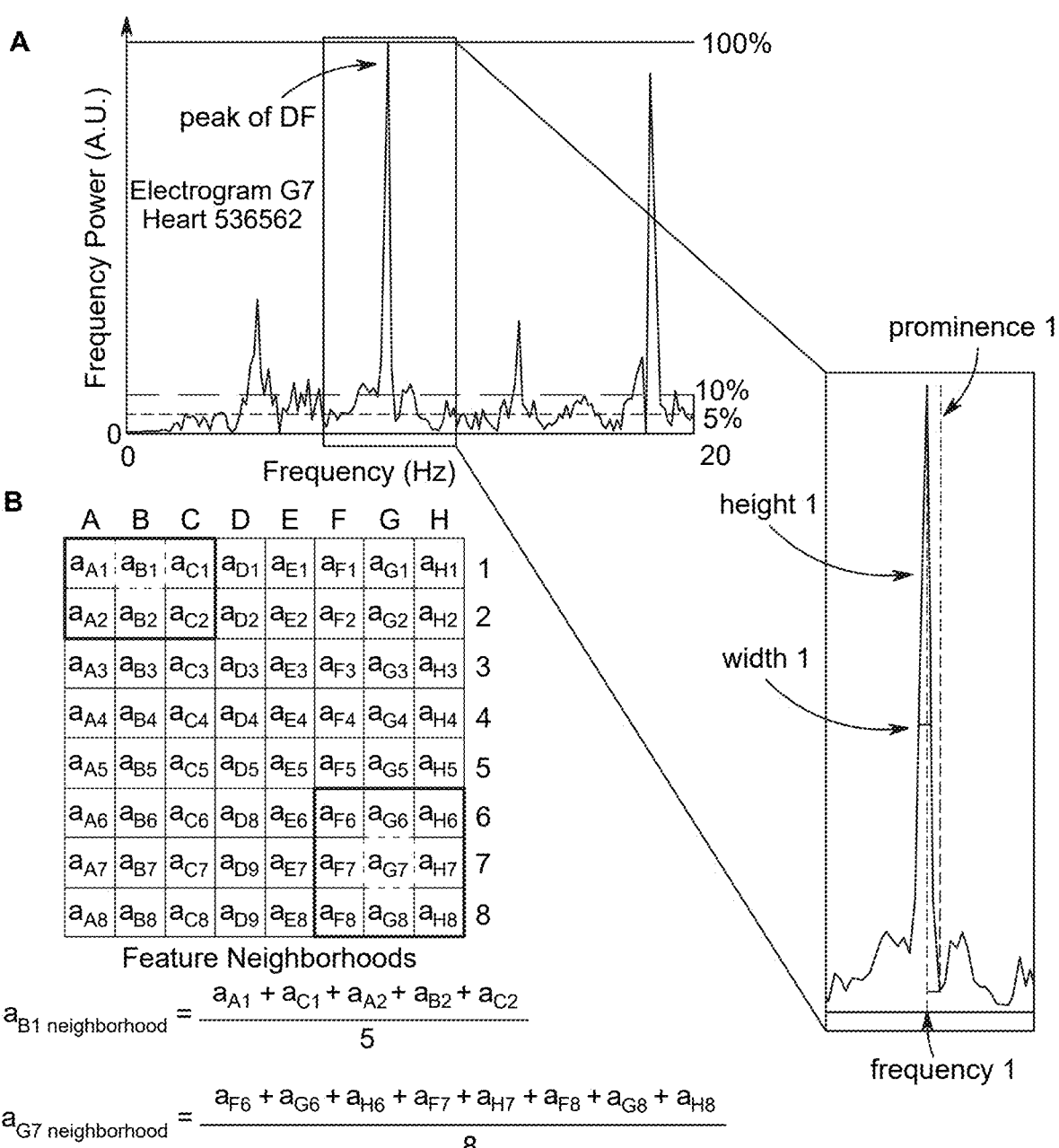
FIG. 2—Feature calculation for an example of a supervised machine learning approach. (A)—Example of Fourier spectra for MEM recording with several of the 35 features labeled. The height of the highest peak (peak of DF) is indicated as solid horizontal line at 100%, the numbers of peaks above two thresholds of 5 and 10% of the highest peak's height (dashed lines) were also used as features for Machine Learning algorithm. (B)—Calculation of the contribution of electrode neighborhood features at each electrode. DF=Dominant Frequency, A.U.=Arbitrary Units.

The integer number n in the feature's name corresponds to the number of the $n^{th}$ highest peak in the Fourier spectrum, ranging from the n=1 peak (the peak of DF) to the n=5 (the fifth highest peak). Spectral features height, width, frequency, and prominence, for each of the five highest peaks, were calculated using scipy.signal library in Python. An example of MEM spectrum and the aforementioned features are shown in FIG. 2A. Features #peaks_0.05 and #peaks_0.1 correspond to the number of peaks higher than a given threshold (5% and 10% of the height of the DF peak, respectively, were chosen) to reflect values of noise present in the recordings. The peak-to-standard deviation ratio (PSDR) feature was calculated as the ratio between the average height of the two highest peaks to the standard deviation of heights across the whole spectrum. The other features are the ratios between features for each of the five tallest peaks.

For a given feature, each "Neighborhood" feature was then generated as a mean of the feature values of the 8 adjacent electrodes in a 3×3 grid, as visualized in FIG. 2B. The examples of Fourier spectra from driver and non-driver neighborhood electrograms and OAPs are shown in FIG. 3. Total number of generated features is equal to 35 for MEM feature sets and 70 for combined MEM+NIOM feature sets.

The above example details one embodiment of the invention. Other embodiments may include the above and any combination of the following alternatives. Other signal processing methods could proceed feature selection based on Goertzel algorithm (Ref. 20), such as a signal derivatives (Ref. 14), Hilbert Transform (Ref. 13), or Sinusoidal Recomposition Phase analysis (Ref. 21).

Example 7. Structural Imaging of Human Atria to Define AF Driver Regions

Figure 4:
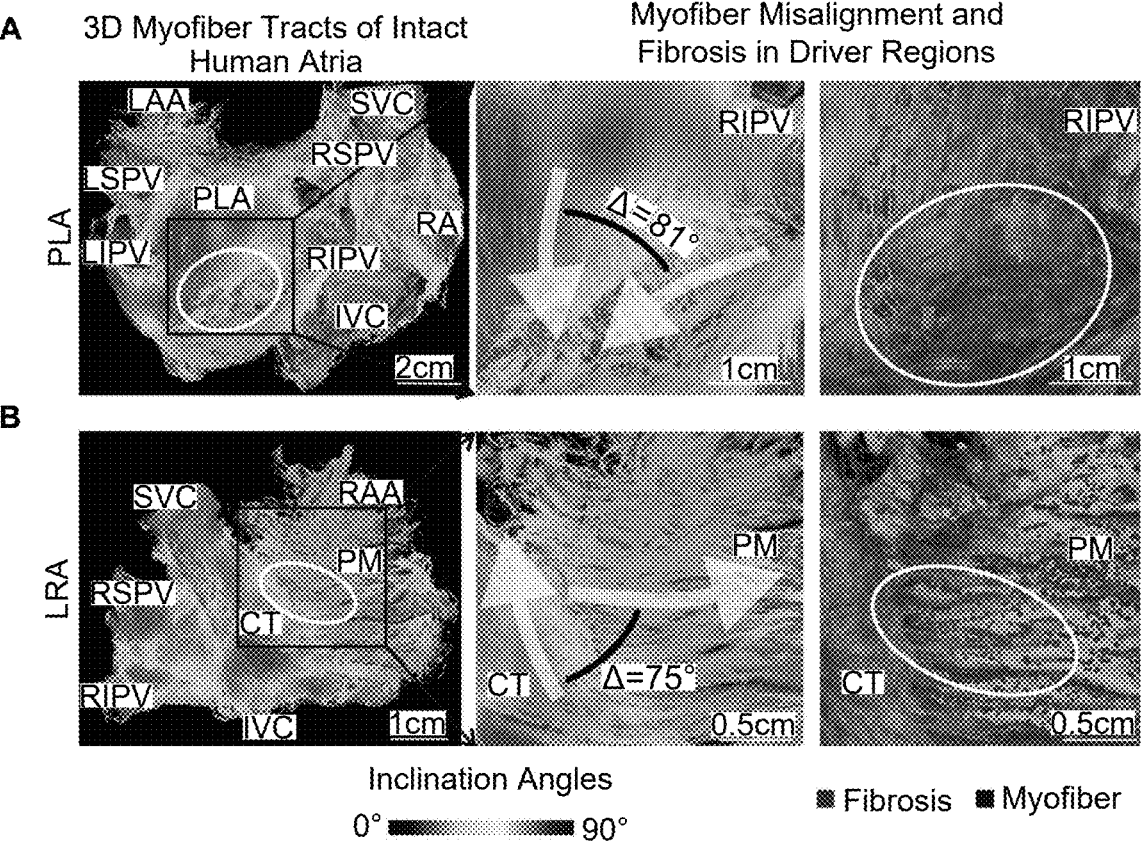

Sources of cardiac arrhythmia may be identified by arrhythmogenic structure. Arrhythmogenic structure is a combination of fibrosis, wall thickness variation, and myofiber orientation or anisotropy (Ref. 11-13). Explanted hearts were scanned with high-resolution gadolinium-based contrast enhanced magnetic resonance imaging (CE-MRI, 155-184 $\mu m^3$) to define detailed human atrial anatomy, 3D fibrosis distribution, myofiber orientation, and wall thickness (FIG. 4) (Ref. 11). CE-MRI-detected fibrosis was defined as gadolinium-enhanced voxels with signal intensity exceeding the threshold, defined by comparing 2D CE-MRI sections with corresponding Masson's trichrome histology sections.

The above example details one embodiment of the invention. Other embodiments may include the above and any combination of the following alternatives. Structural imaging to define driver location by arrhythmogenic structure comprise, without limitation, performing Magnetic resonance imaging (with and without addition of contrast agent, and delayed contrast scans), x-ray computed tomography (with and without addition of contrast agent) (Ref. 22), optical computed tomography, ultrasound imaging (extracorporeal, transesophageal, intracardiac) (Ref. 23).

Example 8. Algorithm Selection and Testing

In one embodiment of the invention, four different AI classification algorithms were tested: k-Nearest Neighbors (kNN), Support Vector Machine (SVM), Scalable Gradient Boosting (XGBoost), and Random Forest (RF). Classification algorithm is a model that can separate unlabeled samples into two classes (binary classification) based on differences in the feature sets. The training/testing sets were randomly obtained from a 70%/30% split of the dataset, with each set having been stratified to provide the same balance of driver and non-driver recordings. Importantly, all windows from one electrogram were allocated to either the training or testing set. In a subset analysis on driver prediction within the electrode array of a full MEM catheter recording, the training sets contained all recordings by a catheter (LD or HD), except for the 64 hold-out recordings from a single 8 by 8 catheter grid for testing. Recordings in the testing set labeled as uninformative were also excluded from the analysis. The algorithm then predicted the labels of each electrode M number of times, with M being equal to the number of the sliding windows from the data sampling step. The final probability of the electrode to be a driver is the mean of the probabilities of each sliding window to be a driver. These probabilities were then visualized as a heatmap, normalizing them from 0 (0% predicted driver probability) to 1 (100% predicted driver probability).

Figure 5:
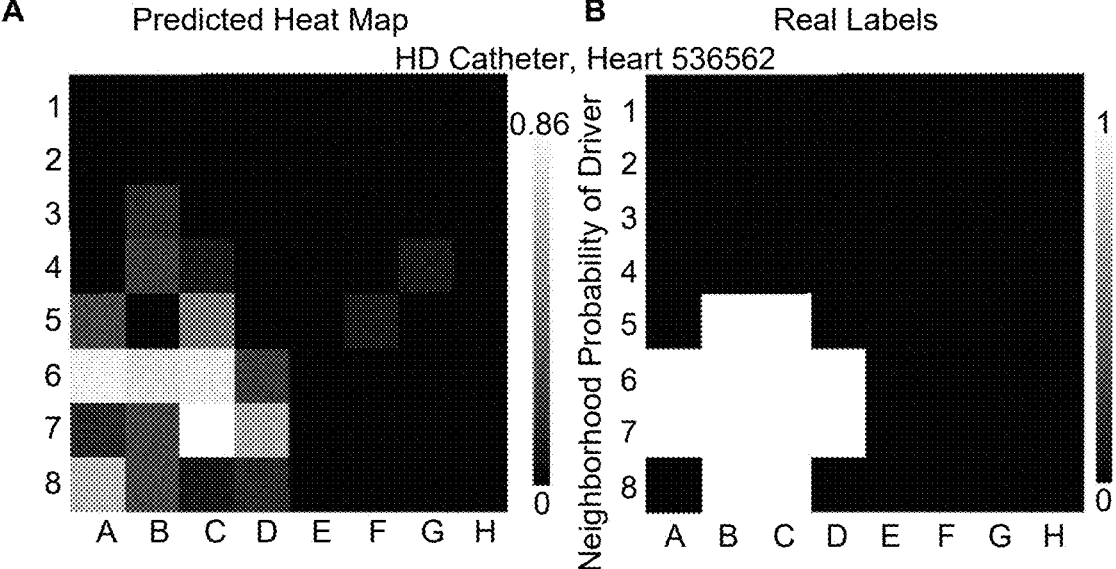
FIG. 5—AF driver prediction by a deep-learning neural network algorithm within an 8×8 electrode array (left) compared to the NIOM-defined gold standard location (right). The grayscale bar encodes probability of an electrode to be a driver.

In another preferred embodiment, the fully-connected Neural Network is used to test the ability of more complicated AI algorithm to separate driver vs non-driver spectra. Neural network has following parameters: 4 hidden layers with batch normalization, learning rate equal to 0.0001, batch size of 64, RMSProp optimizer. The training experiment was carried out for 300 epochs using NVidia CUDA on graphics processor of GeForce 940MX graphics card. The metrics for HD MEM dataset (MEM spectra as inputs) are: accuracy 0.89±0.01, precision 0.83±0.02, recall 0.83±0.02, f1-score 0.83±0.02. The successful arrhythmia source prediction by the neural network algorithm within an 8×8 electrode compared to the NIOM-defined gold standard location is shown in FIG. 5.

The above example details two different embodiments of the invention. Other embodiments may include any combination of the above embodiments and the following alternatives. The AI model can be an AI algorithm selected from the following group: any supervised machine learning binary and multiclass classification and regression algorithms (k-Nearest Neighbors model, Support Vector Machine model, Boosting algorithms, Logistic Regression, Random Forest etc.), neural networks (fully-connected neural networks, convolution neural networks, recurrent neural networks, etc.), or unsupervised (clustering, etc.) algorithms. During pre-training of the AI model, the characterizing features may be selected by a user, for example, for Machine Learning algorithms or may be automatically generated for neural networks or any unsupervised models.

Example 9. Electrogram Collection from Patients with Intent to Treat

Electrograms for the clinical treatment set can be collected from regions of the patient's heart using any commercially available electrogram recording device. Electrograms can be paired to a region of the heart through the use of widely available electroanatomic mapping systems, such as CARTO from Biosense Webster. Electrograms recorded from the patient's heart can come from any commercially available electrode catheter, such as the FIRMap and HD Grid catheters from Abbot EP and the PentaRay or Lasso catheters from Biosense Webster. The term electrode array used throughout this application refers to a device containing one or more electrodes. Electrode arrays can contain electrodes within any geometry with any inter-electrode space. Electrograms recorded for the clinical treatment set can include unipolar and bipolar signals. Electrograms can be recorded from contact, non-contact electrodes and/or body surface electrodes (Ref. 1,2). Electrode arrays used to record the clinical treatment set electrograms can be the same or differ from the electrode arrays used in the training set. Electrograms used in the clinical treatment set can come from a single region of the patient's heart while the electrode array remains stationary or can be come from multiple regions of the patient's heart as the electrode array is moved, as in sequential mapping known in the art (Ref. 17).

Example 10. Performance Metrics

Accuracy, precision, recall, f1-score and area under the curve (AUC) for receiver operating characteristic (ROC) were used in one preferred embodiment disclosed in the previous examples for each AI classification algorithm to evaluate the performance of these performance metrics. Recall (or sensitivity) is the fraction of true positive driver electrodes selected by the algorithm among all possible driver electrodes. Precision (or positive predictive value) is the fraction of true positive drivers selected by the algorithm among all predicted drivers. AUC under ROC shows the prediction performance of the algorithm. f1-score is the harmonic mean of precision and recall, see the formula below.

ROC curve was used to select the best threshold for the binary classification between driver and non-driver recordings. The threshold was chosen to provide the best balance between recall and precision, and the best f1-score:

$$f1-\text{score} = \frac{2 \cdot \text{precision} \cdot \text{recall}}{\text{precision} + \text{recall}}.$$

Then, it was investigated which features are the most valuable for the classification and how few features can be used without suffering a loss in f1-score. The subordinate features were removed until value of f1-score dropped below the original confidence interval.

To carry out the feature importance analysis, an integrated feature importance function from the XGBoost library was used. The results were sorted in the descending order, with the most valuable feature being listed first and the relative contribution of the other features being normalized to the most valuable one.

To assess the possibility to identify the driver region within the whole electrode array, the averaged probability densities per electrode were calculated in the ground-truth location of the driver center plus periphery [$D_{driver}$] and in the background area outside of the driver (the non-driver region) [$D_{outside}$]. The quality of the prediction of the driver in a given part of the array image (given the ground-truth annotation) is then optimally described by the driver contrast formula:

$$\text{Driver contrast} = \frac{D_{driver} - D_{outside}}{D_{driver} + D_{outside}}$$

If the driver contrast is equal to 0, the prediction within the driver annotation mask is not distinguishable from any other region; the higher the contrast is greater than 0, the more easily a user may be able to distinguish the driver region because of the higher probability levels.

Example 11. Statistical Analysis

Metrics in these examples are presented as mean±standard deviation, calculated on 10 folds of the testing set. The performance of the binary classification on the reduced feature set is also reported as mean±confidence interval. The analysis was done using the scipy.stats library in Python. Statistical significance between metrics on different options of feature sets for the same dataset or between metrics on different datasets was analyzed by Tukey's range test for pairwise samples or Repeated Measures ANOVA test for multifactor samples, with the p-value <0.05 being considered as significant. The assumption of the metrics to be sampled from the normal distribution was verified using the Shapiro-Wilk test. A different set of statistical methods may be used in other embodiments of the invention.

Example 12. Samples

In one preferred embodiment disclosed in the previous examples, the final dataset (LD+HD) was assembled consisting of 32 AF episodes in 11 explanted human atria with temporally and spatially stable AF drivers mapped by MEM and NIOM (FIG. 1, Table 3). Each AF episode was mapped by a 64-electrode array, resulting in a total of 32×64=2048 electrogram recordings. This number was expanded using data augmentation by Fourier transformation of window slices of AF recordings, which is widely used in the field (Ref. 18,19). All data were later distributed into 2 datasets (LD or HD) based on catheter resolution.

TABLE 3

Preliminary dataset of explanted human hearts mapped for Examples. LD = Lower-Density catheter, HD = Higher-Density catheter, Epi = Epicardial, Endo = Endocardial, LRA = Lateral Right Atrium, NIOM = Near-infrared optical mapping.

| Heart Code | Preparation | MEM | NIOM | Sample numbers | Driver |
|---|---|---|---|---|---|
| 984478 | Biatrial | LD | Epi | LD_1 | 1 |
| 645444 | LRA | LD | Epi/Endo | LD_2, LD_3 | 1 |
| | | LD | Epi/Endo | LD_4, LD_5 | 2 |
| 728878 | LRA | LD | Endo | LD_6 | 1 |
| | | LD | Epi/Endo | LD_7, LD_8 | 1 |
| 963542 | LRA | LD | Endo | LD_9 | 1 |
| 497522 | LRA | LD | Epi/Endo | LD_10, LD_11 | 1 |
| | | LD | Epi/Endo | LD_12, LD_13 | 1 |
| | | LD | Epi/Endo | LD_14, LD_15 | 2 |
| | | LD | Epi/Endo | LD_16, LD_17 | 1 |
| 994744 | LRA | LD | Epi/Endo | LD_18, LD_19 | 1 |
| | | LD | Epi/Endo | LD_20, LD_21 | 1 |
| 536562 | Biatrial | HD/LD | Endo | HD_1, LD_ 22 | 1 |
| | | HD/LD | Endo | HD_2, LD_23 | 1 |
| 397128 | Biatrial | HD/LD | Endo | HD_3, LD_24 | 1 |
| 642519 | Biatrial | LD | Endo | LD_25 | 1 |
| 228749 | Biatrial | HD | Epi | HD_4 | 1 |
| 373249 | Biatrial | HD | Epi | HD_5 | 1 |
| | | HD | Epi | HD_6 | 1 |
| | | HD | Epi | HD_7 | 2 |

Example 13. Driver vs Non-Driver Classification

Figure 7:
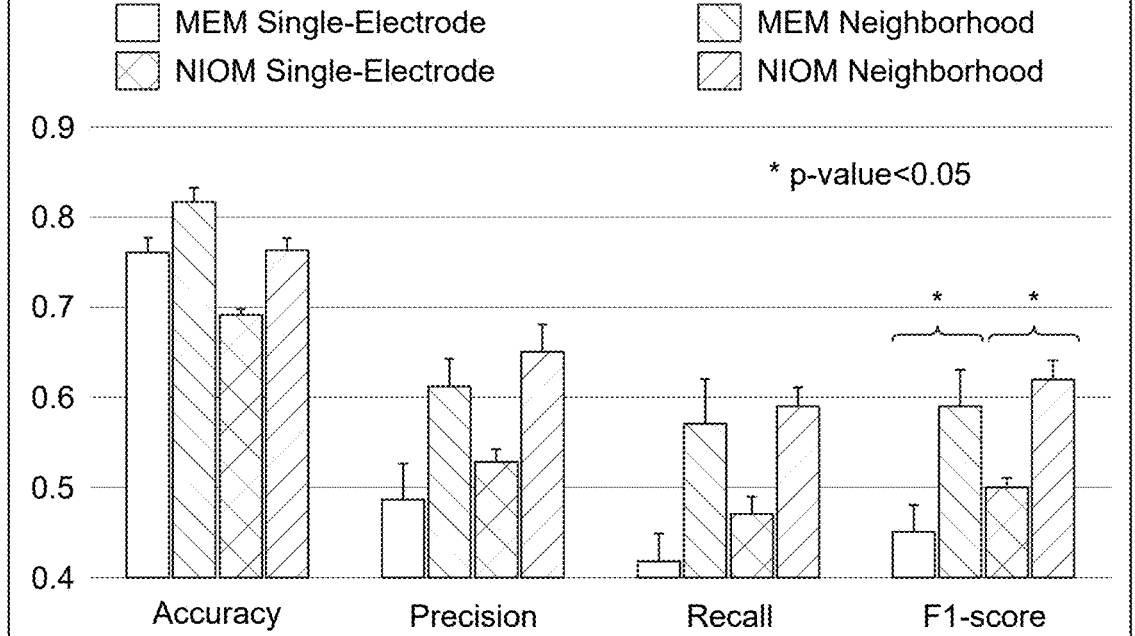
FIG. 7—Comparison between Performance Metrics on Single-Electrode Vs Neighborhood Feature Sets.

In one preferred embodiment disclosed in the previous examples, amongst the 4 MEM frequency feature sets tested with the AI algorithm to classify MEM: single-electrode features of driver center annotation, single-electrode features of driver center plus periphery annotation, electrode-neighborhood features of driver center annotation and electrode-neighborhood features of driver center plus periphery annotation (for all n=35 features); neighborhood electrodes of driver center plus periphery annotation were the best performing. The ROC curves of the 4 AI algorithms considered (kNN, SVM, XGBoost, and RF) for the AF LD+HD dataset are shown in FIG. 6A. kNN accounting for 3 neighbors proved to be the most efficient AI algorithm for the LD+HD dataset with driver center annotation, all 4 algorithms showed comparable f1-scores for driver center plus periphery annotation of LD+HD dataset. The performance metrics (accuracy, precision, recall, and f1-score) for the different feature sets and the highest f1-scores are presented in FIG. 6B. Performance of driver classification could be improved by averaging the features of eight surrounding neighborhood electrodes. FIG. 6B shows that the values of metrics for the electrode-neighborhood feature set are all significantly higher than those for the single-electrode feature set. The similar dynamics were found for NIOM electrode-neighborhood feature set (FIG. 7).

It was also assessed how differences in catheter resolution could affect driver classification (FIG. 8). Resolution was especially important when electrode neighborhoods were considered, as the area of the neighborhood sampled was directly affected by catheter resolution. Though the accuracy corresponding to the HD dataset was approximately equal with the same for LD dataset (89.2±0.5% vs 89.3±1.1% between HD and LD MEM datasets of driver center annotation; 87.5±0.1% vs 87.5±0.2% between HD and LD MEM datasets of driver center plus periphery annotation), other metrics were always higher for the HD dataset. The precision values ranged from 0.26±0.05 for the LD MEM dataset of driver center annotation to 0.78±0.03 for the HD MEM dataset of driver center plus periphery annotation. Furthermore, HD datasets had the highest recall and f1-score (0.84±0.04 and 0.81±0.02 for HD MEM dataset of driver center plus periphery annotation) while LD datasets had the lowest values (0.34±0.08 and 0.30±0.06 for recall and f1-score of LD MEM dataset of driver center annotation, respectively).

Additionally, FIGS. 6 and 8 show that regardless of catheter resolution the center plus periphery driver annotation always resulted in the highest performance metrics in comparison with driver center annotation. Full report on the metrics for all datasets predicted by the 4 AI algorithms can be found in Table 4.

TABLE 4

Statistical performance metrics comparing the binary spectral classifiers including k-Nearest Neighbors (kNN), Scalable Gradient Boosting (XGBoost), Support Vector Machine (SVM), Random Forest (RF) for different datasets and feature sets. Datasets contain samples from low-density catheters (LD), samples from high-density catheters (HD), and a combination of both datasets (HD + LD). Feature sets contain features generated from the spectra of multi-electrode mapping (MEM) samples (MEM single-electrode), combination of features from the spectra of MEM and near-infrared optical mapping (NIOM) samples (MEM + NIOM single-electrode), features from the spectra of electrode-neighborhood MEM samples (MEM electrode-neighborhood), combination of features from the spectra of neighborhood MEM and NIOM samples (MEM + NIOM electrode-neighborhood). All metrics are calculated on 10-folds of the testing set at their optimal ROC threshold computed on the training set.

| Algorithm | | LD center | LD center + periphery | HD center | HD center + periphery | LD + HD center | LD + HD center + periphery |
|---|---|---|---|---|---|---|---|
| | | | | MEM Single-electrode | | | |
| kNN | accuracy | 0.84 ± 0.06 | 0.76 ± 0.03 | 0.84 ± 0.03 | 0.78 ± 0.09 | 0.87 ± 0.03 | 0.76 ± 0.03 |
| | precision | 0.36 ± 0.21 | 0.35 ± 0.11 | 0.63 ± 0.12 | 0.63 ± 0.21 | 0.43 ± 0.19 | 0.44 ± 0.10 |
| | recall | 0.22 ± 0.11 | 0.24 ± 0.08 | 0.46 ± 0.13 | 0.65 ± 0.24 | 0.25 ± 0.10 | 0.35 ± 0.08 |
| | f1-score | 0.27 ± 0.15 | 0.28 ± 0.09 | 0.53 ± 0.12 | 0.63 ± 0.21 | 0.31 ± 0.12 | 0.39 ± 0.09 |
| XGBoost | accuracy | 0.83 ± 0.08 | 0.77 ± 0.04 | 0.74 ± 0.06 | 0.72 ± 0.06 | 0.88 ± 0.02 | 0.77 ± 0.05 |
| | precision | 0.36 ± 0.22 | 0.33 ± 0.11 | 0.37 ± 0.1 | 0.54 ± 0.1 | 0.41 ± 0.13 | 0.48 ± 0.13 |
| | recall | 0.26 ± 0.16 | 0.19 ± 0.1 | 0.4 ± 0.17 | 0.75 ± 0.15 | 0.15 ± 0.07 | 0.28 ± 0.1 |
| | f1-score | 0.28 ± 0.15 | 0.23 ± 0.1 | 0.37 ± 0.12 | 0.62 ± 0.1 | 0.21 ± 0.09 | 0.35 ± 0.11 |
| RF | accuracy | 0.74 ± 0.04 | 0.66 ± 0.03 | 0.70 ± 0.07 | 0.68 ± 0.08 | 0.70 ± 0.06 | 0.77 ± 0.04 |
| | precision | 0.08 ± 0.06 | 0.24 ± 0.06 | 0.34 ± 0.09 | 0.5 ± 0.12 | 0.22 ± 0.07 | 0.52 ± 0.13 |
| | recall | 0.24 ± 0.16 | 0.35 ± 0.12 | 0.5 ± 0.09 | 0.77 ± 0.2 | 0.6 ± 0.16 | 0.23 ± 0.06 |
| | f1-score | 0.12 ± 0.07 | 0.28 ± 0.06 | 0.4 ± 0.09 | 0.6 ± 0.13 | 0.32 ± 0.10 | 0.31 ± 0.08 |

TABLE 4-continued

Statistical performance metrics comparing the binary spectral classifiers including k-Nearest Neighbors (kNN), Scalable Gradient Boosting (XGBoost), Support Vector Machine (SVM), Random Forest (RF) for different datasets and feature sets. Datasets contain samples from low-density catheters (LD), samples from high-density catheters (HD), and a combination of both datasets (HD + LD). Feature sets contain features generated from the spectra of multi-electrode mapping (MEM) samples (MEM single-electrode), combination of features from the spectra of MEM and near-infrared optical mapping (NIOM) samples (MEM + NIOM single-electrode), features from the spectra of electrode-neighborhood MEM samples (MEM electrode-neighborhood), combination of features from the spectra of neighborhood MEM and NIOM samples (MEM + NIOM electrode-neighborhood). All metrics are calculated on 10-folds of the testing set at their optimal ROC threshold computed on the training set.

| Algorithm | | LD center | LD center + periphery | HD center | HD center + periphery | LD + HD center | LD + HD center + periphery |
|---|---|---|---|---|---|---|---|
| SVM | accuracy | 0.89 ± 0.03 | 0.77 ± 0.06 | 0.80 ± 0.02 | 0.79 ± 0.08 | 0.87 ± 0.03 | 0.75 ± 0.04 |
| | precision | 0.15 ± 0.19 | 0.41 ± 0.15 | 0.52 ± 0.16 | 0.66 ± 0.17 | 0.41 ± 0.22 | 0.45 ± 0.09 |
| | recall | 0.09 ± 0.1 | 0.4 ± 0.13 | 0.27 ± 0.13 | 0.66 ± 0.26 | 0.19 ± 0.11 | 0.49 ± 0.11 |
| | f1-score | 0.11 ± 0.12 | 0.4 ± 0.14 | 0.33 ± 0.12 | 0.64 ± 0.19 | 0.26 ± 0.14 | 0.47 ± 0.09 |
| | | | | MEM Neighborhood | | | |
| kNN | accuracy | 0.893 ± 0.011 | 0.875 ± 0.014 | 0.892 ± 0.005 | 0.875 ± 0.016 | 0.902 ± 0.008 | 0.819 ± 0.011 |
| | precision | 0.26 ± 0.05 | 0.69 ± 0.04 | 0.73 ± 0.01 | 0.78 ± 0.03 | 0.55 ± 0.04 | 0.62 ± 0.03 |
| | recall | 0.34 ± 0.08 | 0.63 ± 0.05 | 0.70 ± 0.04 | 0.84 ± 0.04 | 0.52 ± 0.04 | 0.59 ± 0.03 |
| | f1-score | 0.30 ± 0.06 | 0.66 ± 0.04 | 0.72 ± 0.02 | 0.81 ± 0.02 | 0.54 ± 0.04 | 0.60 ± 0.02 |
| XGBoost | accuracy | 0.923 ± 0.008 | 0.866 ± 0.011 | 0.840 ± 0.018 | 0.811 ± 0.014 | 0.902 ± 0.005 | 0.821 ± 0.010 |
| | precision | 0.4 ± 0.1 | 0.84 ± 0.05 | 0.56 ± 0.04 | 0.64 ± 0.02 | 0.60 ± 0.03 | 0.63 ± 0.02 |
| | recall | 0.20 ± 0.06 | 0.37 ± 0.04 | 0.81 ± 0.05 | 0.94 ± 0.02 | 0.31 ± 0.05 | 0.56 ± 0.05 |
| | f1-score | 0.26 ± 0.07 | 0.51 ± 0.05 | 0.66 ± 0.04 | 0.76 ± 0.02 | 0.41 ± 0.05 | 0.59 ± 0.03 |
| RF | accuracy | 0.898 ± 0.004 | 0.807 ± 0.011 | 0.880 ± 0.015 | 0.837 ± 0.020 | 0.886 ± 0.008 | 0.801 ± 0.012 |
| | precision | 0.22 ± 0.04 | 0.50 ± 0.02 | 0.71 ± 0.05 | 0.71 ± 0.03 | 0.47 ± 0.04 | 0.57 ± 0.03 |
| | recall | 0.21 ± 0.05 | 0.57 ± 0.02 | 0.64 ± 0.03 | 0.84 ± 0.03 | 0.43 ± 0.03 | 0.58 ± 0.02 |
| | f1-score | 0.21 ± 0.05 | 0.53 ± 0.01 | 0.67 ± 0.03 | 0.77 ± 0.03 | 0.45 ± 0.03 | 0.57 ± 0.02 |
| SVM | accuracy | 0.915 ± 0.007 | 0.875 ± 0.014 | 0.868 ± 0.016 | 0.866 ± 0.013 | 0.903 ± 0.004 | 0.834 ± 0.009 |
| | precision | 0.24 ± 0.07 | 0.72 ± 0.04 | 0.74 ± 0.06 | 0.80 ± 0.02 | 0.61 ± 0.04 | 0.67 ± 0.02 |
| | recall | 0.13 ± 0.04 | 0.57 ± 0.07 | 0.49 ± 0.06 | 0.77 ± 0.03 | 0.32 ± 0.03 | 0.57 ± 0.03 |
| | f1-score | 0.17 ± 0.05 | 0.64 ± 0.05 | 0.59 ± 0.06 | 0.78 ± 0.02 | 0.42 ± 0.03 | 0.61 ± 0.02 |

Example 14. Feature Importance

Figure 9:
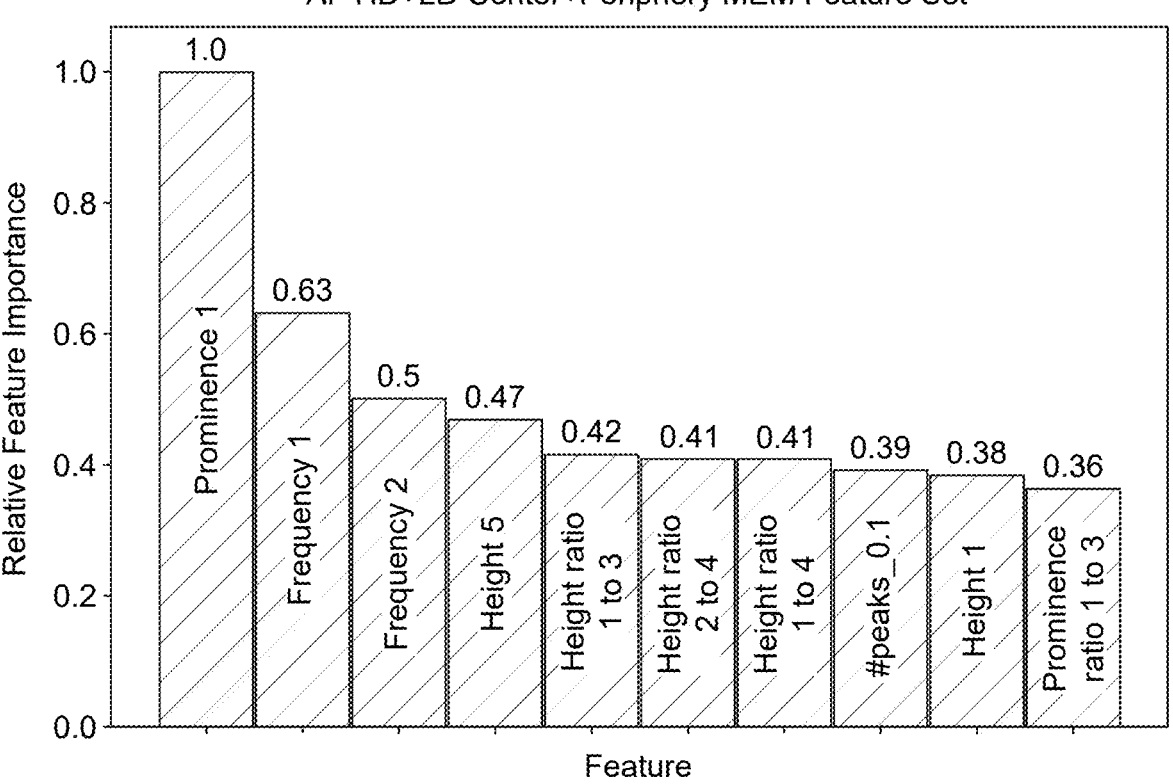
FIG. 9—Relative feature importance of the top 10 most valuable features for neighborhood-electrodes MEM feature sets. Abbreviations as in FIG. 1, PSDR—peak-to-standard deviation ratio.

In one preferred embodiment disclosed in the previous examples, the most valuable features for MEM feature set is listed in FIG. 9. The most valuable feature for the MEM feature set was the relative height (prominence) of the DF, with its frequency and the ratios between the DF height and heights of other peaks among the most valuable features. The features that describe the noise in the spectrum (e.g., signal-to-noise ratio, number of peaks above a threshold, and prominence) were also found to play a vital role in the classification task. The order of the most valuable features slightly varied in different datasets (e.g., LD and HD datasets), the details are summarized in FIG. 10. Importantly, using only the single feature of electrode DF to predict AF driver electrodes had a PPV of 0.31, a sensitivity of 0.26, and an f1-score of 0.28, which emphasizes the importance of our multi-feature AI based approach. It was found that keeping only the 10 most valuable features (out of 35 MEM features) maintained an f1-score within the confidence interval of the full feature set. It should be noticed that other sets of most valuable features may be used or generated in other embodiments of the invention.

Example 15. Driver Localization on the Multi-Electrode Array

In one preferred embodiment disclosed in the previous examples, the ability of AI to outline the location of the AF driver within a simultaneously recorded, clinically-relevant 8×8 electrode array was tested by using the best classification dataset.

Figure 11:
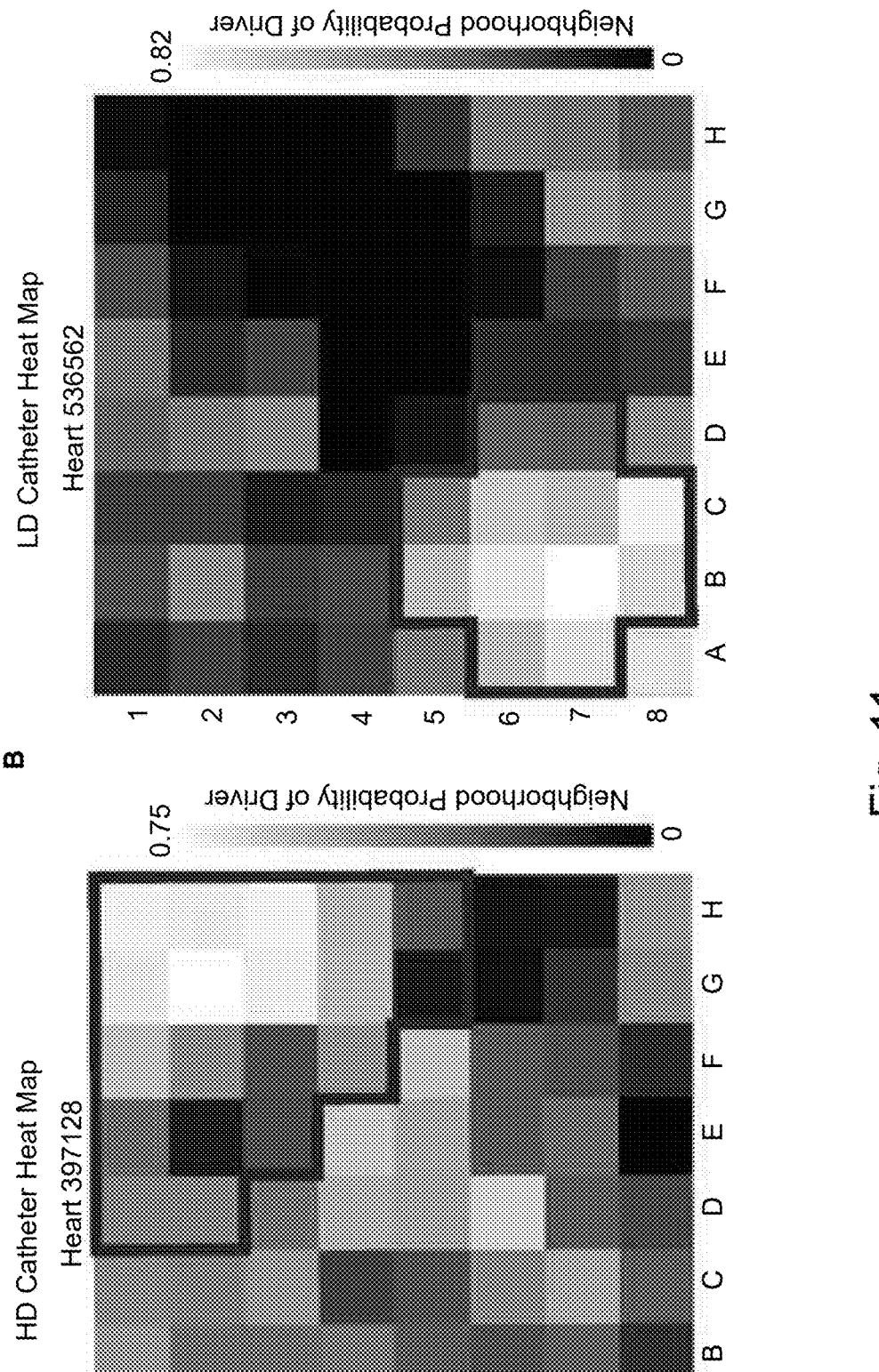
FIG. 11—Examples of the Machine Learning probability prediction heat maps for two 64-electrode catheters—(A) Higher-density (HD) catheter and (B) Lower-density (LD) catheter. Ground truth driver region (center plus periphery) is outlined by black bold line. The grayscale bar encodes probability of an electrode to be a driver.

FIG. 11 shows one example of driver probability heat maps for each catheter set (HD and LD). Subjectively, the AI algorithm pre-trained on electrode neighborhoods and based on driver center plus periphery annotation correctly defined driver area as a region with the highest driver probabilities.

Quantitatively, driver contrast from the background non-driver region demonstrates that the pre-trained algorithm can highlight the driver region for all three datasets with driver contrast higher than zero in 6 out of 7 recordings of HD dataset (87%), in 20 out of 25 recordings of LD dataset (80%), resulting in 26 out of 32 recordings for all AF recordings (81.25% accuracy for combined dataset). Complete results for all recordings are shown in the Table 5.

TABLE 5

Driver contrast for each AF recording
predicted by machine learning algorithm

| Type of catheter | Number of recording | Driver Contrast |
|---|---|---|
| High Density | HD_1 | 0.48 |
| | HD_2 | 0.44 |
| | HD_3 | 0.28 |
| | HD_4 | 0.19 |
| | HD_5 | −0.01 |
| | HD_6 | 0.32 |
| | HD_7 | 0.27 |
| Low Density | LD_1 | 0.48 |
| | LD_2 | 0.21 |
| | LD_3 | 0.35 |
| | LD_4 | 0.18 |
| | LD_5 | −0.02 |
| | LD_6 | 0.02 |
| | LD_7 | 0.06 |
| | LD_8 | 0.10 |
| | LD_9 | 0.70 |
| | LD_10 | 0.37 |
| | LD_11 | 0.02 |
| | LD_12 | −0.07 |
| | LD_13 | 0.12 |
| | LD_14 | 0.29 |
| | LD_15 | 0.41 |
| | LD_16 | −0.13 |
| | LD_17 | 0.22 |
| | LD_18 | 0.22 |
| | LD_19 | 0.44 |
| | LD_20 | −0.04 |
| | LD_21 | 0.39 |
| | LD_22 | 0.62 |
| | LD_23 | 0.73 |
| | LD_24 | −0.20 |
| | LD_25 | 0.20 |

Example 16. Targeted Driver Ablation

In some embodiments, termination of AF to normal sinus rhythm or atrial tachycardia by targeted radiofrequency ablation may be applied endocardially or epicardially to driver path (FIG. 1). Ablation may be targeted to sites along the path of stable repetitive activation with a non-irrigated RFA catheter (for example, 8Fr, 8 mm tip, Lg Cry Blazer II XP, Boston Scientific, MA). RFA was limited at 80 W power and 75° C. temperature for 60 s per location (as described in Ref. 12). Targeted ablation may be used to confirm NIOM-defined AF drivers as the mechanism of sustained AF. The endocardial surface area for targeted ablation (that which terminated AF, converted to atrial tachycardia, or slowed AF by >10%), untargeted ablation (a negative control that was outside the driver region and had no effect on driver dynamics or global AF pattern), and ablation of atrial tachycardia may be calculated relative to total endocardial surface area.

The foregoing outlines examples and embodiments of the methods and systems described and disclosed herein. Those skilled in the art will recognize that many different permutations, combinations and variations of specific methods, AI models, electrode assemblies and so on, are possible without departing from the spirit and scope of the present disclosure. Accordingly, the methods and systems described and disclosed herein are intended to embrace all such alterations, modifications and variations that fall within the scope of the appended claims.

In general, AI techniques are better suited for interpretable predictions when instead of relying on a set of abstract features generated by the machine, the mathematical model is purposely engineered using observable and handpicked, potentially meaningful characteristics of the signal. Unlike agnostic deep learning methods, one can clarify which features are valuable for the classification using a particular feature set, for example, features of the frequency spectra of MEM.

The AI algorithm disclosed here in the Examples allows detection of subtle differences between the features originating from the driver and non-driver regions in the atria as measured by both MEM and NIOM. Similar AI algorithms may be designed to detect subtle differences between the features originating from the source or from the non-source in the case of cardiac arrhythmia of different origin.

Several previous clinical and animal studies show the importance of frequency characteristics in the task of AF driver detection, including instantaneous frequency calculations. Unsurprisingly, it is the DF peak and its characteristics that hold in the provided Examples the greatest classification power in detecting AF driver in the MEM (FIG. 9) feature set. However, a number of studies show the inability of DF, the most common frequency of the signal, to be the sole feature for classification. Confirming this fact, the provided Examples show that the frequencies, heights, and prominences of other highest peaks in the Fourier spectra, as well as the ratios between them, make important contributions to AF driver classifications by AI algorithms. Furthermore, several features of electrogram frequency spectra, aforementioned and noise-related such as PSDR or the number of peaks above some threshold, are critically important in distinguishing drivers from non-drivers. The same will likely be true for detection of other sources of cardiac arrhythmia. If use only the most important 10 features to outline possible driver area, the locations of the highest driver probabilities remain in the same regions of the array and still are inside the ground-truth driver region.

Performance metrics will depend on MEM catheter resolution. An AI model trained on the single-electrode feature may perform below expectations, so it may rely on the features calculated as an average of the electrodes within the surrounding neighborhood. The classifiers based on electrode-neighborhood features provide improved metrics for both MEM and NIOM data (FIG. 6), which suggest the benefit of looking at AF drivers as a region instead of a single point, supported by the ~1.5 cm×0.6 cm average area of reentrant AF drivers previously reported (Ref. 24). Importantly, f1-score, precision, and recall for the binary classification of HD catheter dataset were higher than the metrics of LD catheter dataset, emphasizing the importance of neighborhood resolution in driver classification. One of the reasons for these improvements could be that the average number of driver electrodes per recording was higher for HD compared to LD MEM arrays (17.9±5.5 vs 11.6±2.8 for center plus periphery annotation and 10.9±4.3 vs 4.0±1.3 for only center annotation). The distance between electrodes plays an important role in reentrant AF driver detection by MEM (Ref. 25) as moderate resolution MEMs can miss a part of the driver reentrant track, with NIOM identifying reentrant tracks between and unmapped by widely spread electrode splines.

Traditionally, catheter resolution has been sacrificed for panoramic coverage of the atria, as sequential activation mapping with higher density electrode array is insufficient for driver detection during chaotic AF activation patterns. The AI-based approach developed here could remove the need for activation mapping and allow the use of higher density catheters for improved AF driver identification.

A computing device described here may be implemented as a desktop or laptop computer, a tablet or another similar device. Computing device usually contains the following components: one or more processors, at least one memory, at least one data storage medium, input/output (I/O) interfaces, networking tools, a common data bus. Memory is made usually in the form of RAM and contains necessary program logic that provides the required functionality. The processor executes instructions that are located in the RAM. The data storage medium is usually present in the form of a hard drive, network storage, flash memory, optical storage devices, and others. The data storage medium allows for long-term storage of various types of information, for example, the aforementioned electrogram signals, imaging data, AI algorithms, patient identifiers, etc. The choice of I/O interfaces depends on specifics of the computing device; some standard I/O interfaces include USB, COM, HDMI, PS/2, etc. Networking tools may comprise a device that provides network reception and data transfer, for example, an Ethernet card, WLAN/Wi-Fi module, Bluetooth module, NFC module, GSM modem, etc. An organization of data exchange via a wired or wireless data channel is provided by using networking tools. The examples of data exchange organization are LAN, Intranet, Internet, WAN, WLAN, WMAN or GSM.

In some embodiments, a web-based or cloud infrastructure (e.g., Google Cloud), can be used to implement the disclosed methods. Methods described in this application may be implemented as software code to be executed by a processor using any suitable computer language known in the art. The software code may be stored as a series of instructions or commands on a computer readable medium for storage and/or transmission. A suitable non-transitory computer readable medium can include random access memory (RAM), a hard drive, a compact disk (CD) or a digital versatile disk (DVD), flash memory, and similar products. The computer readable medium may be any combination of such storage or transmission devices.

While various aspects and embodiments have been disclosed herein, the various aspects and embodiments disclosed herein are for purposes of illustration and are not intended to be limiting, with the true scope and spirit being indicated by the following claims.

REFERENCES

1. Terricabras M, Piccini J P, Verma A. Ablation of persistent atrial fibrillation: Challenges and solutions. J Cardiovasc Electrophysiol 2019.
2. Hansen B J, Csepe T A, Zhao J, Ignozzi A J, Hummel J D, Fedorov V V. Maintenance of Atrial Fibrillation: Are Reentrant Drivers With Spatial Stability the Key? Circ Arrhythm Electrophysiol 2016; 9:e004398.
3. Hannun A Y, Rajpurkar P, Haghpanahi M et al. Cardiologist-level arrhythmia detection and classification in ambulatory electrocardiograms using a deep neural network. Nat Med 2019; 25:65-69.
4. Xiong Z, Nash M P, Cheng E, Fedorov V V, Stiles M K, Zhao J. ECG signal classification for the detection of cardiac arrhythmias using a convolutional recurrent neural network. Physiol Meas 2018; 39:094006.
5. Attia Z I, Noseworthy P A, Lopez-Jimenez F et al. An artificial intelligence-enabled ECG algorithm for the identification of patients with atrial fibrillation during sinus rhythm: a retrospective analysis of outcome prediction. Lancet 2019; 394:861-867.
6. McGillivray M F, Cheng W, Peters N S, Christensen K. Machine learning methods for locating re-entrant drivers from electrograms in a model of atrial fibrillation. R Soc Open Sci 2018; 5:172434.
7. Vijayakumar R, Vasireddi S K, Cuculich P S, Faddis M N, Rudy Y. Methodology Considerations in Phase Mapping of Human Cardiac Arrhythmias. Circ Arrhythm Electrophysiol 2016; 9:e004409.
8. Hansen B J, Li N, Helfrich K M et al. First In Vivo Use of High-Resolution Near-Infrared Optical Mapping to Assess Atrial Activation During Sinus Rhythm and Atrial Fibrillation in a Large Animal Model. Circ Arrhythm Electrophysiol 2018; 11:e006870.
9. O'Shea C, Holmes A P, Winter J et al. Cardiac Optogenetics and Optical Mapping—Overcoming Spectral Congestion in All-Optical Cardiac Electrophysiology. Front Physiol 2019; 10:182.
10. Herron T J, Lee P, Jalife J. Optical imaging of voltage and calcium in cardiac cells & tissues. Circ Res 2012; 110:609-23.
11. Zhao J, Hansen B J, Wang Y et al. Three-dimensional Integrated Functional, Structural, and Computational Mapping to Define the Structural "Fingerprints" of Heart-Specific Atrial Fibrillation Drivers in Human Heart Ex Vivo. J Am Heart Assoc 2017; 6.
12. Hansen B J, Zhao J, Csepe T A et al. Atrial fibrillation driven by micro-anatomic intramural re-entry revealed by simultaneous sub-epicardial and sub-endocardial optical mapping in explanted human hearts. Eur Heart J 2015; 36:2390-2401.
13. Hansen B J, Zhao J, Li N et al. Human Atrial Fibrillation Drivers Resolved With Integrated Functional and Structural Imaging to Benefit Clinical Mapping. JACC Clin Electrophysiol 2018; 4:1501-1515.
14. Lou Q, Glukhov A V, Hansen B et al. Tachy-brady arrhythmias: The critical role of adenosine-induced sino-atrial conduction block in post-tachycardia pauses. Heart Rhythm 2013; 10:110-118.
15. Li N, Csepe T A, Hansen B J et al. Adenosine-Induced Atrial Fibrillation: Localized Reentrant Drivers in Lateral Right Atria due to Heterogeneous Expression of Adenosine A1 Receptors and GIRK4 Subunits in the Human Heart. Circulation 2016; 134:486-498.
16. Fedorov V V, Glukhov A V, Ambrosi C M et al. Effects of KATP channel openers diazoxide and pinacidil in coronary-perfused atria and ventricles from failing and non-failing human hearts. J Mol Cell Cardiol 2011; 51:215-225.
17. Liang J J, Elafros M A, Muser D et al. Comparison of Left Atrial Bipolar Voltage and Scar Using Multielectrode Fast Automated Mapping versus Point-by-Point Contact Electroanatomic Mapping in Patients With Atrial Fibrillation Undergoing Repeat Ablation. J Cardiovasc Electrophysiol 2017; 28:280-288.

18. Le Guennec A, Malinowski S, Tavenard R. Data Augmentation for Time Series Classification using Convolutional Neural Networks. In: ECML/PKDD Workshop on Advanced Analytics and Learning on Temporal Data 2016:https://halshs.archives-ouvertes.fr/halshs-01357973.

19. Dehghani A, Sarbishei O, Glatard T, Shihab E. A Quantitative Comparison of Overlapping and Non-Overlapping Sliding Windows for Human Activity Recognition Using Inertial Sensors. Sensors (Basel) 2019; 19.

20. Proakis J G, Manolakis D G. Digital signal processing: principles, algorithms, and applications. 3rd ed. Upper Saddle River, N.J.: Prentice Hall, 1996.

21. Kuklik P, Zeemering S, Maesen B et al. Reconstruction of instantaneous phase of unipolar atrial contact electrogram using a concept of sinusoidal recomposition and Hilbert transform. IEEE Trans Biomed Eng 2015; 62:296-302.

22. Zhao J, Hansen B J, Csepe T A et al. Integration of High-Resolution Optical Mapping and 3-Dimensional Micro-Computed Tomographic Imaging to Resolve the Structural Basis of Atrial Conduction in the Human Heart. Circ Arrhythm Electrophysiol 2015; 8:1514-7.

23. Filippou V, Tsoumpas C. Recent advances on the development of phantoms using 3D printing for imaging with CT, MRI, PET, SPECT, and ultrasound. Med Phys 2018.

24. Csepe T A, Hansen B J, Fedorov V V. Atrial fibrillation driver mechanisms: Insight from the isolated human heart. Trends Cardiovasc Med 2017; 27:1-11.

25. Roney C H, Cantwell C D, Bayer J D et al. Spatial Resolution Requirements for Accurate Identification of Drivers of Atrial Fibrillation. Circ Arrhythm Electrophysiol 2017; 10:e004899.

The invention claimed is:

1. A computer-implemented method for determining a location of a source of cardiac arrhythmia in a patient's heart, comprising at least the steps of:
   a) receiving electrogram signals acquired from a region of the patients' heart using a first set of electrodes; and
   b) applying a pre-trained artificial intelligence (AI) model to predict the location of the cardiac arrhythmia source by using the received signals;
   wherein pre-training of the AI model comprises:
      acquiring electrogram signals from explanted human hearts, said signals are generated by a second set of electrodes assembled into an electrode array that covers at least a part of the explanted human heart, and acquiring co-registered functional and/or structural imaging data in the part of the explanted human heart covered with the electrode array, wherein said functional and/or structural imaging data provide location of at least one source of cardiac arrhythmia;
      processing said electrogram signals and functional and/or structural imaging data to learn characterizing features that will be used in the AI model;
      assigning learned features characterizing electrogram signals generated from at least one electrode on the electrode array to corresponding features characterizing functional and/or structural imaging data generated adjacent to said at least one electrode; and
      classifying features characterizing electrogram signals generated from at least one electrode on the electrode array where functional and/or structural imaging data were acquired as corresponding to a source or to a non-source.

2. The method of claim 1, wherein the source of cardiac arrhythmia is a driver of atrial fibrillation.

3. The method of claim 1, wherein the AI model comprises an AI algorithm selected from the following group: supervised machine learning binary and multiclass classification and regression algorithm, chosen from k-Nearest Neighbors model, Support Vector Machine model, Boosting algorithm, Logistic Regression, or Random Forest; neural network, chosen from fully-connected neural network, convolution neural network, or recurrent neural network; or a unsupervised clustering algorithm.

4. The method of claim 1, wherein during pre-training of the AI model and before assigning, the characterizing features are selected by a user for Machine Learning algorithms or automatically for neural networks or any unsupervised models.

5. The method of claim 1, wherein assigning occurs for features that characterize electrogram signals generated from 3*3 matrix of electrodes located on the electrode array.

6. The method of claim 1, wherein processing of electrogram signals and functional and/or structural imaging data comprises the following steps: generating Fourier transformed electrogram signals and Fourier transformed imaging signals, normalizing signals, band-pass filtering of signals.

7. The method of claim 1, wherein acquiring functional imaging data comprises optical mapping with voltage sensitive dyes, with calcium sensitive dyes, or with fluorescent proteins.

8. The method of claim 1, wherein acquiring structural imaging data comprises performing magnetic resonance imaging, x-ray computed tomography, optical computed tomography, ultrasound imaging.

9. A method for providing a cardiac arrhythmia ablation treatment plan, comprising:
   a) receiving electrogram signals acquired from a region of the patients' heart using a first set of electrodes; and
   b) applying a pre-trained artificial intelligence (AI) model to predict the location of the cardiac arrhythmia source by using the received signals;
   wherein pre-training of the AI model comprises:
      acquiring electrogram signals from explanted human hearts, said signals are generated by a second set of electrodes assembled into an electrode array that covers at least a part of the explanted human heart, and acquiring co-registered functional and/or structural imaging data in the part of the explanted human heart covered with the electrode array, wherein said functional and/or structural imaging data provide location of at least one source of cardiac arrhythmia;
      processing said electrogram signals and functional and/or or structural imaging data to learn characterizing features that will be used in the AI model;
      assigning learned features characterizing electrogram signals generated from at least one electrode on the electrode array to corresponding features characterizing functional and/or structural imaging data generated adjacent to said at least one electrode;
      classifying features characterizing electrogram signals generated from at least one electrode on the electrode array where functional and/or structural imaging data were acquired as corresponding to a source or to a non-source; and
      providing a cardiac arrhythmia ablation treatment plan that includes an ablation of the located source as at least a portion of said cardiac arrhythmia treatment plan.

10. The method of claim 1, wherein acquiring electrogram signals from explanted human hearts comprises simultaneously acquiring electrogram signals and co-registered functional imaging data comprising near-infrared optical mapping from the same explanted human heart.

11. The method of claim 9, wherein acquiring electrogram signals from explanted human hearts comprises simultaneously acquiring electrogram signals and co-registered functional imaging data comprising near-infrared optical mapping from the same explanted human heart.

\* \* \* \* \*